US007135173B2

(12) United States Patent
Bohach et al.

(10) Patent No.: US 7,135,173 B2
(45) Date of Patent: *Nov. 14, 2006

(54) ANTIVIRAL ACTIVITY OF SHIGA TOXIN

(75) Inventors: Carolyn H. Bohach, Moscow, ID (US); Witold A. Ferens, Moscow, ID (US)

(73) Assignee: Idaho Research Foundation, Inc., Moscow, ID (US)

( * ) Notice: Subject to any disclaimer, the term of this patent is extended or adjusted under 35 U.S.C. 154(b) by 32 days.

This patent is subject to a terminal disclaimer.

(21) Appl. No.: 10/325,664

(22) Filed: Dec. 18, 2002

(65) Prior Publication Data

US 2003/0152593 A1 Aug. 14, 2003

Related U.S. Application Data

(63) Continuation-in-part of application No. 09/615,179, filed on Jul. 13, 2000, now Pat. No. 6,541,013.

(51) Int. Cl.
*A61K 38/00* (2006.01)
*A61K 38/16* (2006.01)
*A61K 38/43* (2006.01)
*A61K 39/00* (2006.01)
*A61K 39/02* (2006.01)

(52) U.S. Cl. .................. 424/94.1; 424/236.1; 514/2; 530/300; 530/350

(58) Field of Classification Search ............ 424/178.1, 424/179.1, 183.1, 184.1, 190.1, 192.1, 193.1, 424/194.1, 234.1, 236.1, 241.1, 94.1; 530/300, 530/350, 370, 387.1, 387.3, 395, 402, 403, 530/391.7, 391.9; 536/23.1, 23.2, 23.4, 23.6, 536/23.7; 514/2

See application file for complete search history.

(56) References Cited

U.S. PATENT DOCUMENTS

| | | |
|---|---|---|
| 4,724,205 A | 2/1988 | Karlsson et al. |
| 4,859,769 A | 8/1989 | Karlsson et al. |
| 5,204,097 A | 4/1993 | Arnon et al. |
| 5,220,014 A | 6/1993 | Ackerman et al. |
| 5,378,688 A | 1/1995 | Nett et al. |
| 5,552,144 A | 9/1996 | Samuel et al. |
| 5,552,294 A | 9/1996 | Thorne |
| 5,620,858 A | 4/1997 | Armstrong et al. |
| 5,645,836 A * | 7/1997 | Kitto ............... 424/181.1 |
| 5,679,653 A | 10/1997 | Armstrong et al. |
| 5,744,580 A | 4/1998 | Better et al. |
| 5,747,028 A | 5/1998 | Calderwood |
| 5,756,699 A | 5/1998 | Better et al. |
| 5,762,941 A | 6/1998 | Sansonetti et al. |
| 5,795,717 A | 8/1998 | Nakayama et al. |
| 5,801,145 A | 9/1998 | Gariépy |
| 5,807,879 A | 9/1998 | Rosebrough |
| 5,837,491 A | 11/1998 | Better et al. |
| 5,849,714 A | 12/1998 | Rafter et al. |
| 5,888,750 A | 3/1999 | Vanmaele et al. |
| 5,922,848 A | 7/1999 | Vanmaele et al. |
| 5,955,293 A | 9/1999 | Keusch et al. |
| 5,955,449 A | 9/1999 | Armstrong et al. |
| 5,962,423 A | 10/1999 | Bundle et al. |
| 5,965,128 A | 10/1999 | Doyle et al. |
| 5,965,406 A | 10/1999 | Murphy |
| 5,968,894 A | 10/1999 | Lingwood et al. |
| 5,981,568 A | 11/1999 | Kunz et al. |
| 6,013,506 A | 1/2000 | Wardley et al. |
| 6,015,897 A | 1/2000 | Theodore et al. |
| 6,018,022 A | 1/2000 | Read et al. |
| 6,627,197 B1 * | 9/2003 | Keener et al. ......... 424/183.1 |

OTHER PUBLICATIONS

Basu et al., Infection and Immunity vol. 71 No. 1, pp. 327-334 (Jan. 2003).*
Hino et al., Journal of Infectious Diseases, Colume 157 No. 6, pp. 1270-1271 (Jun. 1988).*
Samuel et al., Journal of Biological Chemistry, vol. 267, No. 7, pp. 4853-4859 (Feb. 1994).*
Haddad et al., Journal of Bacteriology, vol. 175 No. 16, pp. 4970-4978 (Aug. 1993).*
Girbés et al., Journal of Biological Chemistry, vol. 268 No. 24, pp. 18195-18199 (Aug. 1993).*
Al-Jaufy et al., Infection and Immunity, vol. 63 No. 8, pp. 3073-3078 (Aug. 1995).*
Al-Jaufy et al., Infection and Immunity, vol. 62 No. 3, pp. 956-960 (Mar. 1994).*
Skinner et al., Microbial Pathogenesis, vol. 24 No. 2, pp. 117-122 (Feb. 1998).*
Fernández-Puentes et al., Cell, vol. 20 No. 3, pp. 769-775 (Jul. 1980).*

(Continued)

*Primary Examiner*—Bruce R. Campbell
*Assistant Examiner*—Zachariah Lucas
(74) *Attorney, Agent, or Firm*—Christensen O'Connor Johnson Kindness PLLC

(57) ABSTRACT

The present invention provides methods and compositions for eliminating virally-infected cells by administering a Shiga-toxin composition, and the present invention provides methods and compositions for suppressing bovine leukemia-related cell proliferation. In the methods, a Shiga-toxin composition is administered in an amount effective to suppress bovine leukemia-related cell proliferation. The Shiga-toxin composition can include a Shiga-toxin polypeptide; a probiotic microorganism expressing a Shiga-toxin polypeptide; or a transgenic plant expressing a Shiga-toxin polypeptide. In one embodiment, the Shiga-toxin polypeptide is Stx1A and, in another embodiment, the Shiga-toxin polypeptide is Stx1 holotoxin. In yet a further embodiment, the Shiga-toxin polypeptide comprises Stx2.

22 Claims, 8 Drawing Sheets

OTHER PUBLICATIONS

Gatei et al., Journal of Virology, vol. 67 No. 4, pp. 1803-1810 (Apr. 1993).*

Saxena et al., The Journal of Biological Chemistry, vol. 264 No. 1, pp. 596-601 (Jan. 1989).*

Noakes et al., FEBS Letters, vol. 453 Nos. 1-2, pp. 95-99 (Jun. 1999).*

LaCasse et al., Blood, vol. 94 No. 8, pp. 2901-2910 (Oct. 1998).* definition "receptor," Lodish et al., Molecular Cell Biology, Third Edition, Scientific American Books, NY, 1995, p. G-15.* definition "receptor," Wikipedia, the Free Encyclopedia, wikipedia. org. (2005).* definition "receptor," The On-Line Medical Dictionary, cancerweb. ncl.ac.uk/omd. (2003).*

Arroyo, J., et al., "Membrane Permeabilization by Different Regions of the Human Immunodeficiency Virus Type 1 Transmembrane Glycoprotein gp41," *Journal of Virology* 69(7):4095-4102, Jul. 1995.

Austin, P.R., and C.J. Hovde, "Purification of Recombinant Shiga-like Toxin Type I B Subunit," *Protein Expression and Purifications* 6:771-779, 1995.

Austin, P.R., et al., "Evidence That the $A_2$ Fragment of Shiga-Like Toxin Type I is Required for Holotoxin Integrity," *Infection and Immunity* 62(5):1768-1775, May 1994.

Baliga, V., and J.F. Ferrer, "Expression of the Bovine Leukemia Virus and its Internal Antigen in Blood Lymphocytes," *Proceedings of the Society for Experimental Biology and Medicine* 156:388-391, 1977.

Barnett, B., et al., "Antiviral Immunotoxins: Antibody-Mediated Delivery of Gelonin Inhibits Pichinde Virus Replication In Vitro," *Antiviral Research* 15(2):125-138, Feb. 1991.

Bast, D.J., et al., "Murine Antibody Responses to the Verotoxin 1 B Subunit: Demonstration of Major Histocompatibility Complex Dependence and an Immunodominant Epitope Involving Phenylalanine 30," *Infection and Immunity* 65(7):2978-2982, Jul. 1997.

Benigni, F., et al., "Preclinical evaluation of the ribosome-inactivating proteins PAP-1, PAP-S, and RTA in mice," *Int. J. Immunopharmacol.* 17(10):829-839, 1995. (Abstract).

Bodelón, G., et al., "Modification of Late Membrane Permeability in Avian Reovirus-Infected Cells," *Journal of Biological Chemistry* 277(20):17789-17796, May 17, 2002.

Bruck, C., et al., "Biologically Active Epitopes of Bovine Leukemia Virus Glycoprotein GP51: Their Dependence on Protein Glycosylation and Genetic Variablity," *Virology* 136:20-31, 1984.

Carrasco, L., "Modification of Membrane Permeability by Animal Viruses," *Advances in Virus Research* 45:61-112, 1995.

Ciccaglione, A.R., et al., "Mutagenesis of Hepatitis C Virus E1 Protein Affects its Membrane-Permeabilizing Activity," *Journal of General Virology* 82:2243-2250, 2001.

Donohue-Rolfe, A., et al., "Shiga Toxin: Purification, Structure, and Function," *Reviews of Infectious Diseases* 13(Suppl. 4):S293-S297, 1991.

Dosio F., et al., "A New Approach in the Synthesis of Immunotoins: Ribosome Inactivating Protein Noncovalently Bound to Monoclonal Antibody," *Journal of Pharmaceutical Sciences* 83(2):206-211, Feb. 1994.

Driscoll, D.M., et al., "Inhibition of Bovine Leukemia Virus Release by Antiviral Antibodies," *Arch. Virol.* 55(1-2):139-144, 1977.

Ferens, W.A. and C.J. Hovde, "Antiviral Activity of Shiga Toxin 1: Suppression of Bovine Leukemia Virus-Related Spontaneous Lymphocyte Proliferation," *Infection and Immunity* 68(8):4462-4469, Aug. 2000.

Girbés, T., et al., "Recent Advances in the Uses and Applications of Ribosome-Inactivating Proteins From Plants," *Cellular and Molecular Biology* 42(4):461-471, Jun. 1996.

Gupta, p., et al., "Transcriptional Control of the Bovine Leukemia Virus Genome: Role and Characterization of a Nonimmunoglobulin Plasma Protein From Bovine Leukemia Virus-Infected Cattle," *Journal of Virology* 50(1):267-270, 1984.

Hassan, S.H., et al., "Expression and Functional Characterization of Bluetongue Virus VP5 Protein: Role in Cellular Permeabilization," *Journal of= Virology* 75(18):8356-8367, Sep. 2001.

Hovde, C.J., et al., "Evidence That Glutamine Acid 167 is an Active-Site Residue of Shiga-Like Toxin, "*Proc. Natl. Acad. Sci. USA* 85:2568-2572, 1988.

Jensen, W.A., et al., "*In Vitro* Expression of Bovine Leukemia Virus in Isolated B-Lymphocytes of Cattle and Sheep," *Veterinary Immunology and Immunopathology* 26:333-342, 1990.

Kidd, L.C., and K. Radke, "Lymphocyte Activators Elicit Bovine Leukemia Virus Expression Differently as Asymptomatic Infection Progresses," *Virology* 217:167-177, 1996.

Menge, C., et al., "Shiga Toxin 1 From *Escherichia Coli* Blocks Activation and Proliferation of Bovine Lymphocyte Subpopulations *In Vitro,*" *Infection and Immunity* 67(5):2209-2217, May 1999.

Mirsky, M.L., et al., "The Prevalence of Proviral Bovine Leukemia Virus in Peripheral Blood Mononuclear Cells at Two Subclinal Stages of Infection," Journal of Virology 70(4):2178-2183, Apr. 1996.

Paton, A.W., et al., "Neutralization of Shiga Toxins Stx1, Stx2c, and Stx2e by Recombinant Bacteria expressing Mimics of Globotriose and Globotetraose," *Infection and Immunity* 69(3):1967-1970, Mar. 2001.

Pirro, F., et al., "Neutralizing antibodies against Shiga-like toxins from *Escherichia coli* in colostra and sera of cattle," *Veterinary Microbiology* 4343:131-141, 1995.

Portetelle, D., et al., "In Animals Infected by Bovine Leukemia Virus (BLV) Antibodies to Envelope Glycoprotein gp51 Are Directed Against the Carbohydrate Moiety," *Virology* 105:223-233, 1980.

Sandvig, et al., *The EMBO Journal* 19/22:5943-5940, 2000.

Schmidt, H., et al., "A new Shiga Toxin 2 Variant (Stx2f) From *Escherichia coli* Isolated from Pigeons," *Applied and Environomental Microbiology* 66(3):1205-1208, Mar. 2000.

Sparapani, M., et al., "Toxicity of ricin and volkensin, two ribosome-inactivating proteins, to microglia, astrocyte, and neuron cultures," *Glia* 20(3):203-209, 1997.

Stirpe, F., et al., "Ribosome-Inactivating Proteins From Plants: Present Status and Futute Prospects," *Bio/Technology* 10:405-412, Apr. 1992.

Suhan, M.L., and C.J. Hovde, "Disruption of an Internal Membrane-Spanning Region in Shiga Toxin 1 Reduces Cytoxicity," *Infection and Immunity* 66(11):5252-5259, Nov. 1998.

Takashima, I., and C. Olson, "Relation of Bovine Leukosis Virus Production on Cell Growth Cycle," *Archives of Virology* 69(2):141-148, 1981.

Trueblood, E.S., et al., "B-Lymphocyte Proliferation During Bovine Leukemia Virus-Induced Persistent Lymphocytosis Is Enhanced by T-Lymphocyte-Derived Interleukin-2," *Journal of Virology* 72(4):3169-3177, Apr. 1998.

Wachinger, M., et al., "Bryodin, a single-chain ribosome-inactivating protein, selectively inhibits the growth of HIV-1-infected cells and reduces HIV-1 production," *Res. Exp. Med.* 193(1):1-12, 1993. (Abstract).

Watanabe, K., et al., "Actions of pokeweed wntiviral protein on virus-infected protoplasts," *Biosci. Biotechnol. Biochem.* 61(6):994-997, 1997. (Abstract).

Yoshida, T., et al., "Primary cultures of human endothelial cells are susceptible to low doses of Shiga toxins and undergo apoptosis," *J. Infect. Dis.* 180(6):2048-2052, 1999. (Abstract).

Zandomeni, R.O., et al, "Induction and inhibition of bovine leukemia virus expression in naturally infected cells," *Journal of General Virology* 73:1915-1924, 1992.

Zhang, W., et al., "Identification, Characterization, and Distribution of a Shiga Toxin 1 Gene Variant ($stx_{1c}$) in *Escherichia coli* Strains Isolated from Humans," *Journal of Clinical Microbiology* 40(4):1441-1446, Apr. 2002.

Zollman, T.M., et al., "Purification of Recombinant Shiga-Like Toxin Type I $A_1$ Fragment From *Escherichia coli,* " *Protein Expression and Purification* 5:291-295, 1994.

* cited by examiner

Stx1A      −    +

ANTIVIRAL ACTIVITY OF SHIGA TOXIN

CROSS-REFERENCE TO RELATED APPLICATION

This application is a continuation-in-part of U.S. application Ser. No. 09/615,179, filed Jul. 13, 2000, now U.S. Pat. No. 6,541,013 incorporated herein by reference in its entirety.

This invention was made with government support awarded by the National Institutes of Health (grant numbers AI33981, NO1-HD-03309, and P20RR15587) and by the U.S. Department of Agriculture (NRICGP grants 95-37201-1979 and 99-35201-8539). The government has certain rights in the invention.

FIELD OF THE INVENTION

The present invention relates to methods and compositions for eliminating virally-infected cells using a Shiga-toxin polypeptide and to methods and compositions for suppressing bovine leukemia virus-related lymphocyte proliferation using a Shiga-toxin polypeptide.

BACKGROUND OF THE INVENTION

Bovine Leukemia Virus (BLV) is an oncogenic retrovirus responsible for the enzootic form of bovine lymphosarcoma, the most frequent malignancy of domestic cattle (Ferrer (1980 *Adv. Vet. Sci. Comp. Med.* 24:1–68). BLV infection results in a 1–8 year long asymptomatic period (Ferrer et al. (1979) *J. Am. Vet. Med. Assoc.* 175(7):705–8), followed by development of persistent lymphocytosis (PL) in approximately 30% of infected cattle with progression to a malignant lymphosarcoma in fewer than 10% of the animals (Ferrer et al. (1979) *J. Am. Vet. Med. Assoc.* 175(7):705–8). The PL stage is a benign neoplasia of B lymphocytes, which are the predominant or exclusive targets of BLV (Esteban et al. (1985) *Cancer Res.* 45(7):3225–30). This stage of infection is associated with an increased percentage of peripheral B lymphocytes containing provirus as well as increased viral gene expression (Mirsky et al. (1996) *J. Virol.* 70(4):2178–83). The development of PL markedly enhances the probability of transmission (Mammerickx et al. (1987) *Leuk Res.* 11:353–58). The critical importance of PL to transmission of this blood-borne disease was demonstrated by experiments showing that it required significantly less blood from cattle with persistent lymphocytosis to transmit BLV than blood from infected cattle which did not have persistent lymphocytosis (Mammerickx et al. (1987) *Leuk. Res.* 11:353–58). Moreover, vertical transmission from BLV-infected dams to their calves has been shown to be strongly correlated with persistent lymphocytosis (Agresti et al. (1993) *Amer. J. Vet. Res.* 54:373–78).

In cattle, the ability to transmit BLV varies (Weber et al. (1983) *Amer. J. Vel. Res.* 44:1912–15); Marnmerickx et al. (1987) *Leuk. Res.* 11:353–58), and expression of antigen after in vitro culture has been shown to correlate with infectivity (Miller et al. (1985) *Amer. J. Vet. Res.* 46:808–13). The level of BLV expression in the animal also may correlate with the probability of development of persistent lymphocytosis (Cockerell et al. (1988) *Leuk. Res.* 12:465–69; Dropulic et al. (1992) *J. Virol.* 66:1432–41). Moreover, persistent lymphocytosis is a strong risk factor for development of lymphoma. In 1–10% of the animals with persistent lymphocytosis, B cell clones undergo neoplastic transformation, leading to leukemia or lymphoma, and cattle with persistent lymphocytosis are three times more likely to develop lymphoma than infected cattle without persistent lymphocytosis (Ferrer et al. (1979) *J. Am. Vet. Med. Assoc.* 175(7):705–8).

BLV is prevalent in dairy operations, with up to 89% of the U.S. dairy operation seropositive for BLV (Howie (1997) *Feedstuffs* 69:11). Not only does the virus kill cattle, milk and fat yields in BLV-infected cows with persistent lymphocytosis are greatly reduced (Da et al. (1993) *Proc. Natl. Acad. Sci. U.S.A.* 90:6538). Moreover, BLV also produces malignant lymphomas in sheep (Wittman et al. (1989) *Arch. Exp. Veterinaermed.* 23:709). However, the greatest economic impact of BLV infection in the United States arises from the fact that several countries will not import cattle from BLV-infested areas. Although various attempts have been made to develop a vaccine against BLV infection, an effective vaccine to protect cattle or sheep is not available (Miller et al. (1978) *Annales de Recherches Veterinaires* 9:871; U.S. Pat. No. 4,323,555). BLV infection is thus a costly impediment to cattle production.

Peripheral blood mononuclear cells (PBMC) from BLV-infected cattle proliferate spontaneously in vitro (Takashima & Olson (1981) *Arch. Virol.* 69(2):141–8; Thorn et al. (1981) *Infect. Immun.* 34(1):84–9). This spontaneous lymphocyte proliferation (SLP) is particularly vigorous in PBMC cultures from cattle in the PL stage of infection. Derepression of viral gene transcription and the synthesis of viral proteins precede SLP (Kettmann et al. (1976) *Proc. Natl. Acad. Sci. USA.* 74(4)1014–18; Baliga & Ferrer (1977) *Proc. Soc. Exp. Biol. Med.* 156(2):388–91; Ferrer (1980) *Adv. Vet. Sci. Comp. Med.* 24:1–68). Therefore, SLP provides a tractable model system for identifying factors that are capable of preventing BLV-induced neoplasia and malignant lymphoma in infected cattle. The present invention shows that Shiga-toxin type 1 (Stx1) is a potent and selective inhibitors of BLV-induced SLP. The present invention also shows that Shiga-toxin type 2 (Stx2) is a potent and selective inhibitors of BLV-induced SLP.

The family of Shiga toxins includes Stx type 1 (Stx1), Stx type 2 (Stx2) and Stx type 2 variants (Donahe-Rolfe et al. (1991) *Rev. Infect. Dis.* 13(Suppl. 4):S293–7). These toxins belong to a large family of ribosome-inactivating proteins (RIPs) that are found in a variety of higher plants and some bacteria. Most RIPs are hemitoxins (enzymatically active A chains) and some are holotoxins (one A chain associated with a specific number of B changes. Thus, class 1 RIPs (hemitoxins) are N-glycosidases that inactivate ribosomes by removing a single adenine in a specific ribosomal RNA sequence (Endo et al. (1987) *J. Biol. Chem.* 262:5908–12; Endo et al. (1988) *Europ. J. Biochem.* 171:45–50). Class 2 RIPs (holotoxins) are composed of an A subunit homologous to class 1 RIPs, noncovalently joined to one or more B subunits, usually galactose-specific lectins, that facilitate toxin binding and uptake into target cells. Holotoxins are highly toxic to cells expressing receptors for B subunit(s), but not to receptor-deprived cells, and are not toxic to normal cells as isolated A chains (Barnett et al. (1991) *Antiviral. Res.* 15:125–38; Dosio et al. (1994) *J. Pharm. Sci.* 83:206–11; Girbes et al. (1996) *Cell. Mol. Biol. (Noisy-legrand)* 42:461–71). Plant hemitoxins are not toxic to the plants that synthesize them and have low cytotoxicity against animal cells, unless the cells have high pinocytic activity (Change et al. (1979) *Contraception* 19:175–84; Yeung et al. (1988) *Int. J. Pept. Protein Res.* 31:265–8).

Plant RIPs of both class 1 (e.g., pokeweed antiviral protein, titrin, trichosanthin) and class 2 (e.g., ricin) have potent antiviral activities (Stirpe et al. (1992) *Biotechnology*

(NY) 10:405–12). These compounds often inhibit viral proliferation in mammalian cells in vitro, and some have been tested in vivo in clinical or laboratory settings. For example, plant hemitoxins can enter and eliminate virally-infected plant cells, and some are also found to be highly toxic to various virally-infected animal cells (Girbes et al. (1996) *Cell Mol. Biol.* (Noisy-le-grand) 42:461–71). The class 2 RIP ricin can eliminate latent herpes simplex virus in mice (Hino et al. (1988) *J. Infect. Dis.* 157(6):1270–1). Other plant RIPs inhibit replication of human immunodeficiency virus type 1 (HIV1) in human peripheral blood mononuclear cells at concentrations nontoxic to uninfected cells (Olson et al. (1991) *AIDS Res. Hum. Retroviruses* 7(12)1025–1030; Lee-Huang et al. (1995) *Proc. Natl. Acad. Sci. U.S.A.* 92(19):8818–22).

Shiga toxins are class 2 RIPs composed of an A subunit associated with a pentamer of receptor-binding B subunits. Because of their ability to bind to target cells, class 2 RIPs are potent cytotoxins. Stx1 is toxic to cells that express high levels of the toxin receptor, globotriosylceramide (Gb3 or CD77), most notably Vero cells and human glomerular endothelial cells (Jackson (1990) *Microbial. Pathogenesis* 8:235–42).

One problem associated with using RIPs as general antiviral agents is their specificity (Wachinger et al. (1993) *Res. Exp. Med.* 193(1):1–12; Watanabe et al. (1997) *Biosci. Biotechnol. Biochem.* 61:994–997). For example, the RIP Bryodin selectively inhibits the growth of HIV-1-infected cells, whereas RIPs gelonin and ricin did not (Wachinger et al. (1993) *Res. Exp. Med.* 193(1):1–12). Another concern is that RIPs are highly cytotoxic (Benigni et al. (1995) *Int. J. Immunopharmacol.* 17:829–39; Sparapani et al. (1997) *Glia* 20:203–9; Yoshida et al. (1999 *J. Infect. Dis.* 180:2048–52). Therefore, although the antiviral effects of some RIPs are known, the use of RIPs as antiviral agents has not been generally applicable. Surprisingly, it has been discovered that Stx1 strongly inhibits BLV-related cell proliferation and BLV expression and does not cause indiscriminate cell death (Ferens & Hovde (2000) *Infect. Immun.* 68:4462–9). Specifically, this activity is manifested by subunit A of Shiga-toxins, which is nontoxic to ruminants or humans.

SUMMARY OF THE INVENTION

The present invention provides methods and compositions for eliminating cells infected with virus by the administration of Shiga-toxin polypeptides. In one aspect, the invention provides methods for eliminating virally-infected cells in a mammalian subject, including administering to a mammalian subject infected with a virus an amount of a Shiga-toxin composition effective to eliminate virally-infected cells. In another embodiment, the invention provides methods for treating a virus infection in a mammal, including administering to a mammal infected with a virus an amount of a Shiga-toxin composition effective to treat the virus infection. The administration of the Shiga-toxin polypeptide can prevent or treat the manifestations of viral infections.

The Shiga-toxin composition may include Stx1, Stx2, or Stx variants, or combinations thereof. The Shiga-toxin composition may include one or more holotoxins or the A subunit of one or more Shiga-toxins, or combinations thereof. In some embodiments, the virally-infected cells are infected with an animal virus, such as semliki forest virus, vesicular stomatitis virus, vaccinia, adenovirus, polio virus, picoma virus, togavirus, reovirus, respiratory syncitial virus, hepatitis virus, coronavirus, rotavirus, influenza virus, herpes virus, and immunodeficiency viruses (e.g., human or bovine immunodeficiency viruses). The mammalian subjects may be ruminants, such as sheep. Alternatively, the mammalian subjects may be other mammals, such as rodents, cats, dogs, horses, monkeys, and humans.

The present invention provides methods and compositions for suppressing BLV-related lymphocyte proliferation. The method utilizes a composition that provides a Shiga-toxin polypeptide having antiviral activity.

In one aspect, a method for suppressing BLV-related lymphocyte proliferation is provided. In the method, the proliferation of BLV-infected cells is suppressed by administering an amount of a Shiga-toxin polypeptide having antiviral activity effective to suppress BLV-related lymphocyte proliferation. The administration of the Shiga-toxin-polypeptide can prevent or treat the manifestations of BLV infection. In one embodiment, a purified Shiga-toxin polypeptide having antiviral activity is administered. In another embodiment, a naturally occurring microorganism expressing a Shiga-toxin polypeptide having antiviral activity is administered. In a further embodiment, a Shiga-toxin-expressing microorganism that has been modified to eliminate expression of the B subunit of the holotoxin is administered. In yet another embodiment, a microorganism that has been modified to express a Shiga-toxin polypeptide having antiviral activity is administered. In another embodiment, a transgenic plant that has been modified to express a Shiga-toxin polypeptide having antiviral activity is administered.

In another aspect of the invention, compositions for delivering a Shiga-toxin polypeptide are provided. In one embodiment, the invention provides a microorganism genetically modified to express a Shiga-toxin polypeptide having antiviral activity. In another embodiment, a Shiga-toxin-expressing microorganism that has been modified to eliminate expression of the B subunit of the holotoxin is provided. In a further embodiment, a transgenic plant genetically modified to express a Shiga-toxin polypeptide having antiviral activity is provided. In yet another embodiment, a composition is provided that includes a naturally occurring microorganism that expresses a Shiga-toxin polypeptide.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 4 illustrates the effect of Stx1A on the expression of BLV protein in cultured PBMC from BLV-positive cows. PBMC were harvested after 12 hr of culture with or without 1.0 µg/ml Stx1A, washed cells were lysed and blotted onto nitrocellulose. The blot was probed with monoclonal antibody against BLV p24 core protein. Sample obtained prior to culture (0 hr) shows p24 protein in unstimulated ex vivo PBMC.

FIGS. 5A and 5B show a comparison of enzymatic and antiviral activity of Stx2, three mutant toxins, and Stx1A in protein synthesis (FIG. 5A) and cell proliferation (FIG. 5B) inhibition assays. Rabbit reticulocyte lysates were pre-incubated with various amounts of Stx1A, Stx2 holotoxin, A:B association mutant (Stx1A$_1$), enzymatic mutant (E167D), cell-trafficking mutant (A231G-D234E), or with no toxin and these lysates were then used in a luciferase protein synthesis assay. Toxin enzymatic activity was expressed as a percent of control and was calculated by dividing the amount of luciferase made by lysates incubated with toxin by the amount of luciferase made by lysates without toxin. PBMC from BLV-positive cattle were cultured for 72 h with various amounts of Stx1A, Stx2 holotoxin, or with no toxin. Antiviral activity was expressed as a percent of control, and was calculated by dividing the amounts of $^3$H-thymidine incorporated by PBMC cultured with toxins by the amounts incorporated by PBMC cultured without toxin. Data are means±SE from two experiments performed in duplicate (protein synthesis inhibition) or four experiments performed in quadruplicate (PBMC proliferation).

FIGS. 6A and 6B show the effect of Stx1A and the enzymatic mutant E167D on BLV expression by cultured PBMC from BLV-positive cattle. PBMC from BLV-positive cattle were cultured with 1.0 µg/ml of Stx1A, enzymatic mutant E167D, or without toxin and were harvested at 24, 48, and 72 h post-culture. Cells (FIG. 6A) and culture supernatants (FIG. 6B) were assayed for BLV proteins p24 and gp51 expression by blotting the lysed cells or cell-free culture supernatants onto nitrocellulose and probing with mouse monoclonal antibodies to p24 and gp51, followed by anti-mouse Ig antibody conjugated to alkaline phosphatase. Blots were developed using 5-bromo-4-chloro-3-indolylphosphate and nitroblue tetrazolium as substrate, and the reaction intensities were quantified using a densitometer. PBMC from BLV-negative cattle were used as controls. The experiment was performed four times with PBMC from three BLV-positive cattle, and a representative experiment is shown.

DETAILED DESCRIPTION

Figure 1:
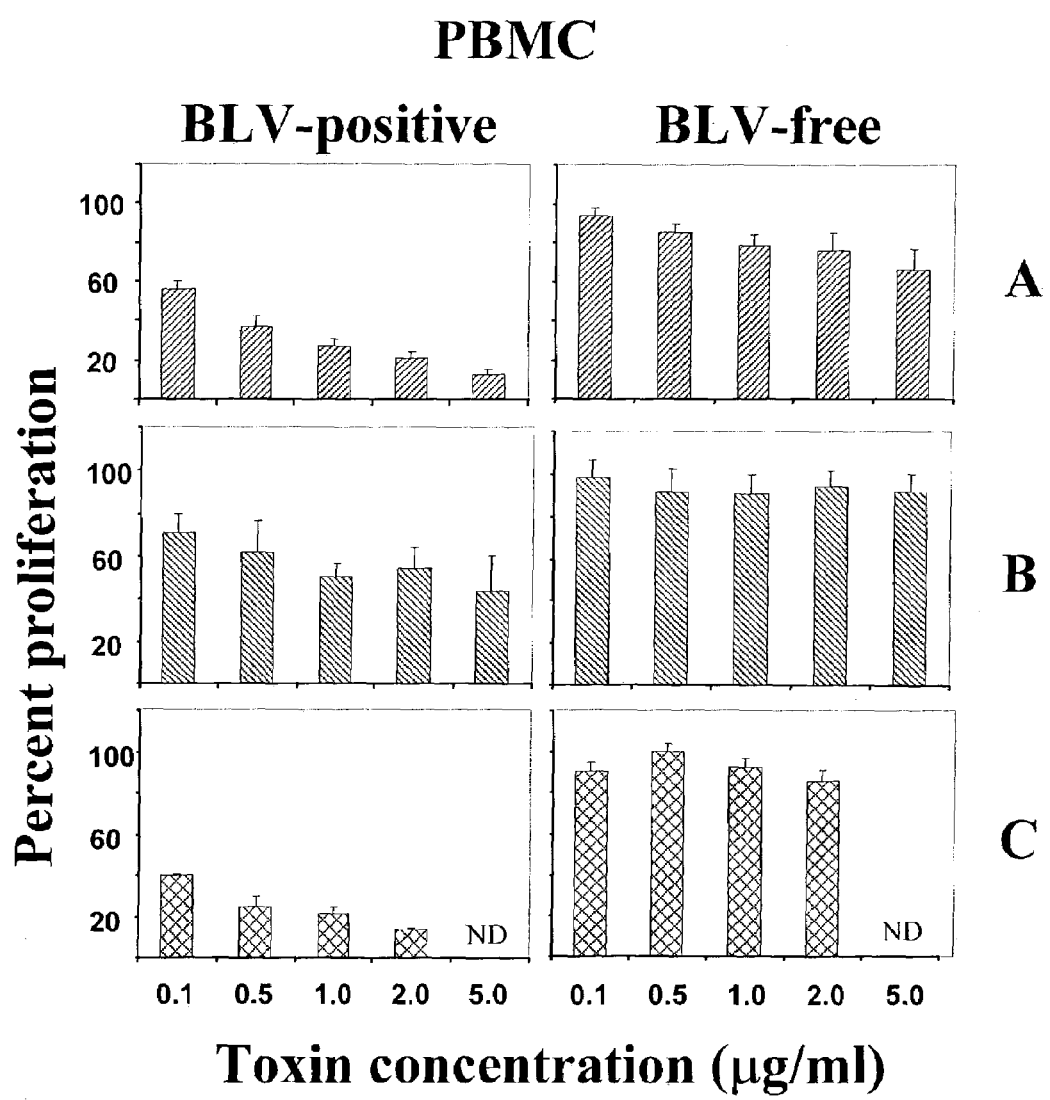
FIGS. 1A–1C illustrate the effect of Stx1 on lymphocyte proliferation. PBMC from persistently lymphocytotic (BLV-positive) or healthy (BLV-negative) cows were incubated with Stx1 holotoxin or subunits. (A, A subunit; B, B subunit; and C, holotoxin). BLV-negative cells were induced to proliferate by pokeweed mitogen (5.0 µg/ml). Cell proliferation was measured as incorporation of tritiated thymidine and expressed as a percentage of the cell proliferation in identical cultures without toxin. Data are means±standard error from three (holotoxin) or ten (Stx1 subunits) experiments. ND refers to not done.

Abbreviations used are as follows:

| | |
|---|---|
| BLV | bovine leukemia virus |
| PL | persistent lymphocytosis |
| SLP | spontaneous lymphocyte proliferation |
| PBMC | peripheral blood mononuclear cells |
| Stx1 | Shiga-toxin type 1 holotoxin |
| Stx2 | Shiga-toxin type 2 holotoxin |
| Stx1A | Shiga-toxin type 1 subunit A |
| Stx1B | Shiga-toxin type 1 subunit B |
| Stx2A | Shiga-toxin type 2 subunit A |
| Stx2B | Shiga-toxin type 2 subunit B |

The present invention provides methods and compositions for eliminating virally-infected cells by administering a Shiga-toxin polypeptide having antiviral activity. Virally infected cells, for example cells infected by semliki forest virus, vesicular stomatitis virus, vaccinia, adenovirus, polio virus, picoma virus, togavirus, reovirus, coronavirus, rotavirus, influenza virus, herpes virus, and immunodeficiency viruses, often exhibit increased permeability to macromolecules due to virus-induced alterations in cell membrane (reviewed in Carrasco (1995) Adv. Virus Res. 45:61–112). This effect has been attributed to the presence of viral gene products (see, e.g., Hassan et al. (2001) J. Virol. 75(18): 8356–67; Bodelon et al. (2002) J. Biol. Chem. 277(20): 17789–96). For example, the transmembrane glycoprotein gp41 of human immunodeficiency virus type 1 (HIV-1) enhances the permeability of cell membranes to the antibiotic hygromycin B even when expressed at low levels (Arroyo et al. (1995) *J. Virol.* 69(7):4095–4102). The M2 protein of influenza virus has also been shown to increase permeability of cells to a number of hydrophilic molecules (Guinea & Carrasco (1994) FEBS Lett. 343(3):24206). Similarly, the p10 protein of reovirus induces an increase in the permeability of the host membrane (Bodelon et al. (2002) *J. Biol. Chem.* 277(20):17789–96). Other examples of viral proteins causing increased membrane permeability include the small hydrophobic protein of human respiratory syncitial virus (Perez et al. (1997) *Virology* 235(2):342–51), poliovirus polypeptide 3AB (Lama & Carrasco (1996) *J. Gen. Virol.* 77(9):2109–119), the E1 glycoprotein of hepatitis virus C (Ciccaglione et al. (2001) *J. Gen. Virol.* 82(9): 2243–50), and the VP5 protein of Bluetongue virus (Hassan et al. (2001) *J. Virol.* 75(18):8356–67). The present invention shows that cells infected with bovine leukemia virus also exhibit increased membrane permeability (see EXAMPLE 5). These cells are eliminated upon exposure to Shiga-toxin compositions (see EXAMPLES 1, 4, and 5).

Thus, present invention provides methods and compositions for eliminating cells infected with virus by the administration of Stx polypeptides. In one aspect, the invention provides methods for eliminating virally-infected cells in a mammalian subject, including administering to a mammalian subject infected with a virus an amount of a Shiga-toxin composition effective to eliminate virally-infected cells. In another embodiment, the invention provides methods for treating a virus infection in a mammal, including administering to a mammal infected with a virus an amount of a Shiga-toxin composition effective to treat the virus infection.

The Shiga-toxin composition may include Stx1, Stx2, or Stx variants, or combinations thereof. The Shiga-toxin composition may comprise one or more holotoxins or the A subunit of one or more Shiga toxins, or combinations thereof. In some embodiments, the virally-infected cells are infected with an animal virus, such as semliki forest virus, vesicular stomatitis virus, vaccinia, adenovirus, polio virus, picorna virus, togavirus, reovirus, respiratory syncitial virus, hepatitis virus, coronavirus, rotavirus, influenza virus, herpes virus, and immunodeficiency viruses (e.g., human or bovine immunodeficiency viruses). The mammalian subjects may be ruminants, such as sheep. Alternatively, the mammalian subjects may be other mammals, such as rodents, cats, dogs, horses, monkeys, or humans.

The present invention provides methods and compositions for suppressing BLV-related cell proliferation by administering a Shiga-toxin polypeptide having antiviral activity. In one aspect of the invention, methods for suppressing BLV-related lymphocyte proliferation are provided. In the methods, an amount of Shiga-toxin polypeptide effective to suppress BLV-related lymphocyte proliferation is administered. In one embodiment, a Shiga-toxin composition is administered to an animal subject in an amount effective to (1) prevent or treat BLV-induced persistent lymphocytosis, (2) to prevent or treat BLV-induced malignant lymphoma, (3) to eliminate BLV-expressing cells, (4) to slow the progression of BLV infection, or (5) to inhibit BLV transmission from infected to uninfected animals. The Shiga-toxin polypeptide includes the portion of the toxin that imparts antiviral activity to the polypeptide. In one embodiment, the Shiga-toxin polypeptide is the subunit A of Stx1. In a further embodiment, the Shiga-toxin polypeptide is the subunit A of Stx2. In another embodiment, the Shiga-toxin polypeptide is the Stx1 holotoxin. In yet another embodiment, the Shiga-toxin polypeptide is the Stx2 holotoxin.

Amounts of a Shiga-toxin composition or polypeptide effective to eliminate virally-infected cells generally include any amount sufficient to eliminate virally-infected cells as detected by any assay described herein or known in the art. Similarly, amounts of a Shiga-toxin composition or polypeptide effective to treat a viral effection includes any amount sufficient to eliminate virally-infected cells, or reduce or alleviate one or more symptoms of a viral infection as detected by any assay described herein or known in the art. Thus, effective amounts of Shiga-toxin polypeptide generally include any amount sufficient to detectably suppress BLV-related lymphocyte proliferation by any of the assays described herein, by other assays known to those having ordinary skill in the art, or by detecting an alleviation of symptoms in a subject infected with BLV.

In one embodiment, the method provides a method for suppressing BLV-related cell proliferation by contacting cells with a Shiga-toxin polypeptide having antiviral activity. In the method, an amount of Shiga-toxin polypeptide effective to suppress BLV-related cell proliferation is administered.

The Shiga-toxin polypeptide can administered in several forms. In one embodiment, a Shiga-toxin polypeptide is administered in a purified form. In another embodiment, a Shiga-toxin polypeptide is provided by a probiotic microorganism. The microorganism can be either a naturally-occurring microorganism that expresses a Shiga-toxin polypeptide having antiviral activity, or a microorganism that has been modified to express a Shiga-toxin polypeptide having antiviral activity. The probiotic microorganism can be modified to express a Shiga-toxin polypeptide having antiviral activity that does not include the B subunit of the holotoxin. In another embodiment, a Shiga-toxin polypeptide is provided by a transgenic plant modified to express a Shiga-toxin polypeptide having antiviral activity.

In another aspect of the invention, compositions for delivering a Shiga-toxin polypeptide are provided. The Shiga-toxin polypeptide can be administered in a purified form along with an acceptable carrier. Alternatively, the Shiga-toxin polypeptide can be administered by way of an organism that expresses the polypeptide. In one embodiment, a Shiga-toxin polypeptide is produced by a probiotic microorganism modified to express a Shiga-toxin polypeptide having antiviral activity. In another embodiment, a Shiga-toxin polypeptide is produced by a plant modified to express a Shiga-toxin polypeptide having antiviral activity.

As used herein, the following terms have the meanings defined below:

The term "Shiga-toxin polypeptide" refers to a polypeptide from the Shiga-toxin type 1 family of ribosome-inactivating proteins having antiviral activity as measured by the suppression of proliferation of BLV-infected cells. The term also applies to Shiga-toxin type 2 polypeptides or Stx variants. Members of the Stx family are differentiated by their biological activity, cross-reactivity with Stx1 or Stx2 antisera, binding affinity for the glycolipid receptor $Gb_3$, and/or sequence analysis (see Schmidt et al. (2000) *Appl. Env. Microbiol.* 66(3):1205–08; Zhang et al. (2002) *J. Clin. Microbiol.* 40(4):1441–6; Paton et al. (2001) *Infect. Immun.* 69(3):1967–70). Examples of Stx variants are Stx2c, Stx3d, Stx2e, Stx2f, and Stx1c (Schmidt et al. (2000) *Appl. Env. Microbiol.* 66(3):1205–08; Zhang et al. (2002) *J. Clin. Microbiol.* 40(4):1441–6). All Stx types associated with human disease (Stx1, Stx2, Stx2c, and Stx2d, recognize the same glycolipid receptor, $Gb_3$ (see Paton et al. (2001) *Infect. Immun.* 69(3):1967–70). Shiga-toxin polypeptides can include a portion or all of either subunit A alone, or in combination with subunit B (e.g., the Stx1 holotoxin). The term also refers naturally occurring forms of Shiga-toxin polypeptides as well as modified derivatives thereof having antiviral activity. The Shiga-toxin polypeptides may be naturally occurring in *E. coli*, or in any other organism (e.g., a bacterium or a virus) that produces Shiga-toxins, for example, *Shigella*. A partial Shiga-toxin polypeptide coding sequence will suffice for antiviral activity. A minimal essential coding sequence(s) for a functional Shiga-toxin polypeptide can be determined, for example, by synthesis and evaluation of subsequences comprising the native Shiga-toxin polypeptide, and by site-directed mutagenesis studies of the Shiga-toxin polypeptide coding sequence. Moreover, the term "Shiga-toxin polypeptide" includes fusion proteins in which Shiga-toxin polypeptide sequences are fused to heterologous sequences to improve levels of expression, stability, and the like.

The term "Shiga-toxin composition" refers to any composition containing a Shiga-toxin polypeptide having antiviral activity. For example, it includes Shiga-toxin polypeptides in partially or completely purified form, and in the form of a probiotic microorganism or a transgenic plant expressing a Shiga-toxin polypeptide. Anti-viral activity may be determined using the assay for the suppression of spontaneous lymphocyte proliferation disclosed herein. The Shiga-toxin composition can include an acceptable carrier for effective delivery. The nature of the carrier can depend on the delivery method.

The term "probiotic microorganism" refers to a live microbial feed supplement which beneficially affects the host animal by improving its intestinal microbial balance (see Fuller (1989) *J. Appl. Bacteriol.* 66:365–78). Recent speculations suggest that "genetic engineering offers the possibility of using microbes to deliver specific actions or products to the colon or other mucosal surfaces . . . other fertile areas for future study include defining the mechanisms of action of various biotherapeutic agents with the possibility of applying genetic engineering to enhance activities" (Elmer et al. (1996) *J. Am. Med. Assoc.* 275: 870–76). Elmer et al. (1996) further point out that the terms "probiotic" and "biotherapeutic agent" have been used in the literature to describe microorganisms that have antagonistic activity toward pathogens in vivo; those authors more specifically prefer the term "biotherapeutic agent" to denote "microorganisms having specific therapeutic properties." The present invention teaches a novel type of "probiotic" or "biotherapeutic" treatment using specifically engineered strains of microorganisms provided herein which do not occur in nature. Nonetheless, available teachings concerning selection of optimal microbial strains, in particular bacterial strains, for conventional probiotic or biotherapeutic applications can be employed in the context of the present invention.

The term "plant" refers to whole plants, plant organs (e.g., leaves, stems, flowers, roots, etc.), seeds and plant cells (including tissue culture cells), and progeny of same. The class of plants that can be used in the method of the invention is generally as broad as the class of higher plants amenable to transformation techniques, including both monocotyledonous and dicotyledonous plants, as well as certain lower plants such as algae. Suitable plants include plants of a variety of ploidy levels, including polyploid, diploid and haploid. The term "transgenic plant" refers to a plant modified to express a Shiga-toxin polypeptide.

The term "eliminating virally-infected cells" refers to any reduction in the number of cells that are infected with the virus. The term "treatment," as used herein, refers to reducing or alleviating symptoms of viral infection. For example, treatment refers to reducing or alleviating symptoms of BLV infection in a ruminant, preventing symptoms from worsening or progressing, inhibiting BLV expression of propagation, eliminating BLV-infected cells, or preventing the infection or symptom in a ruminant that is free therefrom. Thus, for example, treatment includes destruction of bovine leukemia viruses, inhibition of or interference with its expression or propagation, neutralization of its pathological effects and the like. As used herein, the term "treatment" also refers to prophylactic administration of a Shiga-toxin composition. A disorder is "treated" by partially or wholly remedying the cause of the disorder.

As noted above, the present invention provides methods and composition for the suppression of proliferation of BLV-infected lymphocytes using a Shiga-toxin polypeptide having antiviral activity. In one aspect of the invention, a Shiga-toxin polypeptide is provided to BLV-infected lymphocytes in cultures of peripheral blood mononuclear cells (PBMC) from infected cows.

PBMC from five BLV-positive cows in the persistently lymphocytotic stage of infection invariably proliferated in vitro, and this SLP was consistently suppressed by Stx1 (FIG. 1). Holotoxin or the A subunit alone (Stx1A) were potent suppressors of SLP, acting in a dose-dependent manner over the range of concentrations tested. Compared to Stx1A, the B subunit (Stx1B) was far less potent in suppressing SLP even with molar concentrations of Stx1B more than 4-fold higher than Stx1A. Moreover, in contrast to Stx1A, Stx1B did not act in a dose-dependent fashion. Anti-Stx1A immune serum neutralized Stx1 or Stx1A activity in a dose-dependent manner (FIG. 2) and did not affect cellular proliferation in cultures without toxin. The result confirms that that the suppression was due to Stx1 and not due to some spurious inhibitor present in the toxin preparations.

In contrast to SLP, proliferation of BLV-free PBMC induced by poke weed mitogen was only weakly sensitive to Stx1 (FIG. 1). Moreover, the suppression of SLP by Stx1 did not diminish the ability of B-cells in BLV-positive PBMC cultures to respond to immunostimulation by interleukin-2 or poke weed mitogen (Table 1). Especially relevant is the fact that Stx1 was a potent SLP inhibitor at low concentrations, which had only marginal impact on normal PBMC. The result implies that Stx1 suppresses SLP via a selective mechanism and is consistent with the fact that very few B cells in BLV-infected cattle express viral proteins or viral particles (Gupta et al. (1984) *J. Virol.* 50(1):267–70).

Figure 3:
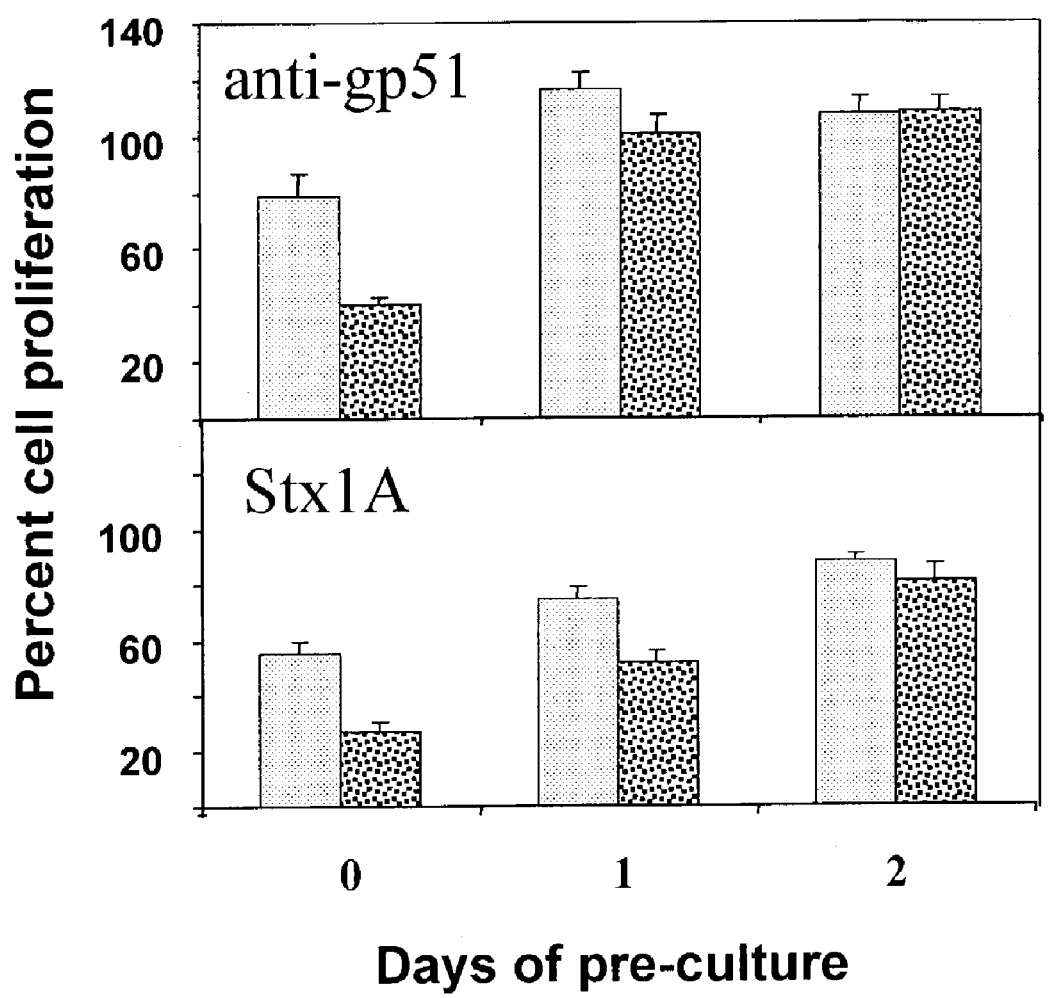
FIG. 3 illustrates the effect of pre-culture on the ability of anti-BLV antibody or the Stx1 subunits to inhibit SLP in cultures of PBMC from persistently lymphocytotic (BLV-positive) cows. Anti-gp51 monoclonal antibody or toxins were added to PBMC cultures on day 0 (without pre-culture) or after PBMC had been precultured for 1 or 2 days in medium. Antibody was applied at 2.0 µg/ml (light stipple) and 20.0 µg/ml (dark stipple). Toxins were applied at 0.1 µg/ml (light stipple) and 1.0 µg/ml (dark stipple). Cell proliferation was measured as incorporation of tritiated thymidine and expressed as a percentage of the cell proliferation in control cultures treated with PBS. Data are means±SE from three or more experiments.

SLP in cultures of BLV-positive PBMC is preceded within 24 hr of culture by de novo synthesis of viral proteins and dissemination of viral particles (Baliga & Ferrer (1977) *Proc. Soc. Exp. Biol. Med.* 156(2):388–91). The expression of BLV particles in culture reaches maximum after 12 to 24 hr of cell culture (Zandomeni et al. (1992) *J. Gen. Virol.* 73(8):1915–24). It is known that anti-BLV serum can block SLP (Thorn et al. (1981) *Infect. Immun.* 34(1):84–9; Trueblood et al. (1998) *J. Virol.* 72(4):3169–77). This possibly results from the interference with the release of BLV particles from cultured cells (Driscoll et al. (1977) *Arch. Virol.* 55(1–2):139–44). To assess whether viral proteins accessible to antibody were required to sustain SLP, the ability of antiviral antibody to interfere with SLP over a two-day period was examined. Antiviral antibody was able to reduce thymidine incorporation in spontaneously proliferating cultures by 60% (FIG. 3). However, this inhibition required application of antiviral antibody at the beginning of cell culture (FIG. 3). These results are in agreement with the findings that dissemination of BLV proteins is involved in initiation of SLP, but the results also suggest that BLV proteins are not required for continuation of an established SLP event. Similar to treatment with antiviral antibody, the ability of Stx1A to inhibit SLP was reduced when cells were precultured in medium for 24 hours before toxin application (FIG. 3). These results indicate that inhibition of SLP by Stx1A is time-dependent, and may be based on the ability of the toxin to interfere with the initiation of spontaneous proliferation. The fact that susceptibility of SLP to inhibition by either Stx1A or antiviral antibody lessens within 24 hours of culture evidences that the cells involved in dissemination of viral proteins and the initiation of SLP constitute targets for Stx1.

Figure 4:
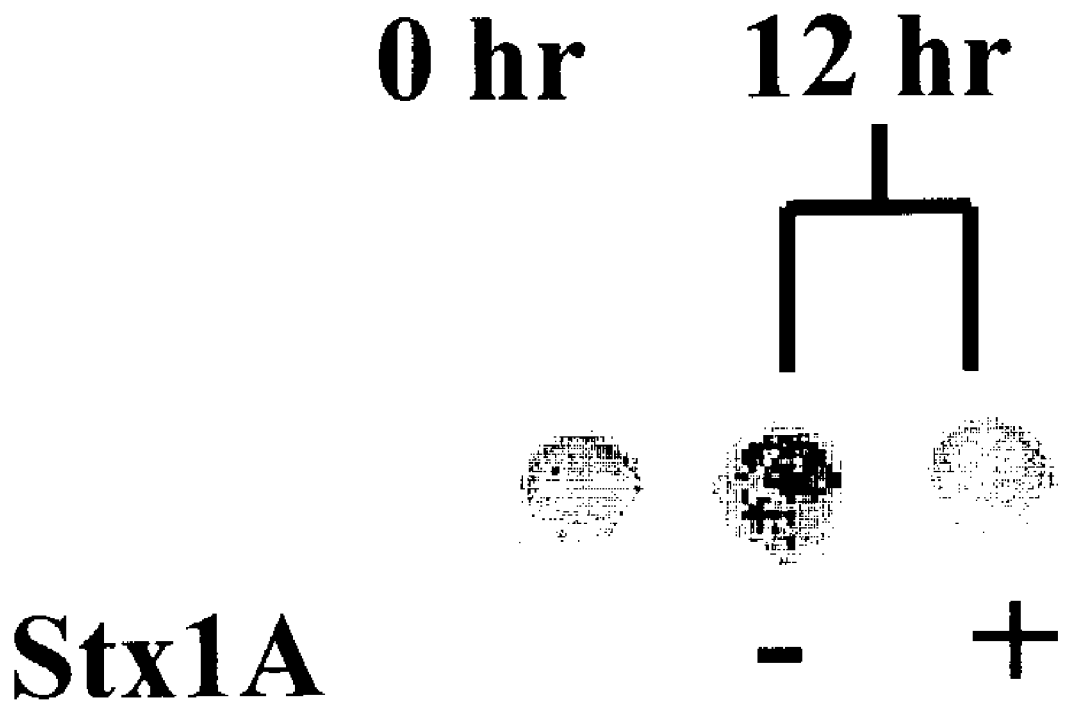

The expression of BLV p24 core protein in PBMC cultured with Stx1A was significantly reduced. Analysis of cell lysates of PBMC cultured for 12 hr showed a 442-fold reduction in the amount of p24 protein in cells treated with toxin compared to cells in the control cultures without toxin (FIG. 4). The reduced expression of BLV p24 protein in cell cultures treated with Stx1 could be due either to the nonlethal suppression of viral protein synthesis or Stx1-mediated lysis of the cells expressing viral proteins. In a further experiment, cell-associated BLV proteins were prominent in control cultures not treated with toxin, apparent in cultures treated with the enzymatic mutant E167D, but barely detectable in cultures treated with Stx1A (see EXAMPLE 4, FIG. 6A). In contrast to BLV protein expression associated with cells, the cell-free supernatants from cultures incubated with toxins contained either similar amounts (48 h) or greater amounts (72 h) of BLV proteins, compared to control cultures (FIG. 6B). The finding that Stx1A-treated cultures harvested at 48 h and 72 h contained small amounts of BLV proteins associated with cells but high amounts of BLV proteins in the culture supernatants suggests that the interaction of Stx1A with target cells interrupted virion assembly, induced cell death and/or loss of membrane integrity.

SLP of BLV-positive PBMC is also suppressed by Stx2 (see EXAMPLE 4 and FIG. 5), indicating that Stx1 and Stx2 have similar enzymatic and antiviral properties. The enzymatic activity of Stx is necessary for antiviral activity. For example, mutants that retained undiminished enzymatic activity (Stx1A$_1$ and A232D-G234E) suppressed SLP as effectively as wild type Stx1A, as described in EXAMPLE 4. However, the molecular motifs required for receptor-mediated cytotoxicity of Shiga-toxins were not necessary for antiviral effect.

In summary, these results demonstrate that SLP of BLV-positive PBMC is suppressed by Shiga-toxins and that the inhibitory effect is mediated by the A subunit of holotoxin. These results provide a demonstration of both the antiviral activity of Shiga-toxins, and the suppression of BLV expression and BLV-associated cell proliferation by this family of toxins. Moreover, the results are consistent with previous research showing that other members of the RIP family of toxins possess antiviral activity against specific viruses (reviewed in Stirpe et al. (1992) Bio-Technology 10:405–412).

The most likely explanation for the inhibitory effect is that Stx1 has an adverse impact on the cells that express the virus. Very little information exists regarding the action of Stx1 on bovine cells. A recent publication (Menge et al. (1999) Infect. Immun. 67(5):2209–17) describes the impact of Stx1 on the metabolic rate of normal bovine PBMC. The study showed that the metabolism of PBMC was reduced by Stx1A but only if the cultures were first stimulated by mitogens. Menge et al. (Menge et al. (1999) Infect. Immun. 67(5):2209–17) did not detect any cytotoxic impact of Stx1 on PBMC, even when Stx1 caused 50% reduction of the metabolic rate. The reference does not clarify the BLV status of their PBMC donors, it is possible that the effects observed were due to antiviral activity of Stx1.

Figure 7:
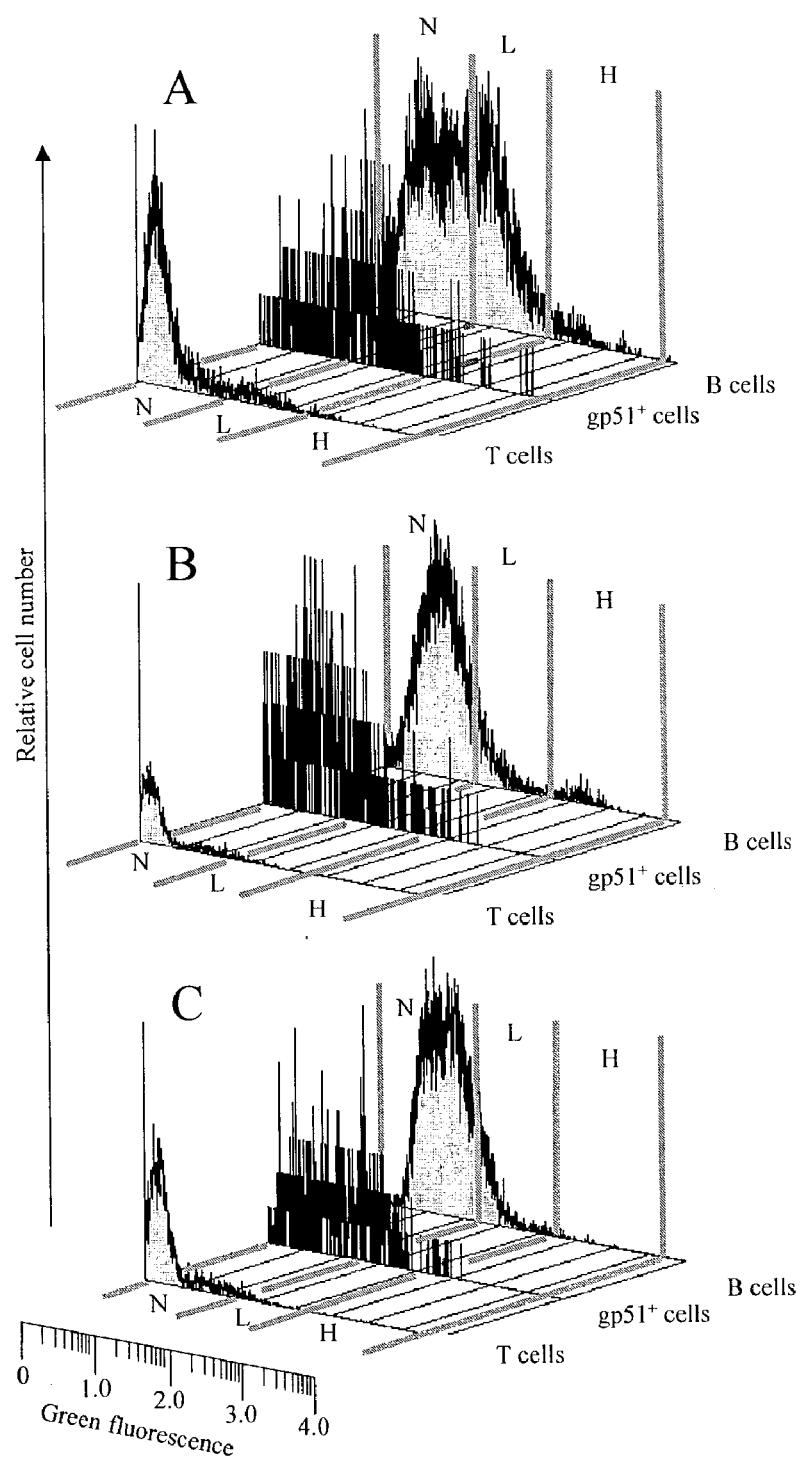
FIGS. 7A–7C show the permeability of T cells, B cells, and gp51-positive PBMC from BLV-positive cattle. PBMC from BLV-positive cattle were incubated for one h with fluorescein-conjugated dextrans (green fluorescence) of 3 kDa (FIG. 7A), 40 kDa (FIG. 7B), or 70 kDa (FIG. 7C) and analyzed by flow cytometry. Lymphocyte subpopulations were identified on the basis of staining with Tri-Color labeled monoclonal antibodies (red fluorescence) as T cells (positive for bovine CD3 and comprising 26% of the total cells), B cells (positive for CD21-like antigen and comprising 48% of the total cells), and gp51-positive cells (BLV-expressing cells, positive for viral gp51 antigen and comprising 1.6% of the cells) (designation at right of each graph). Cells were assessed for dextran content by green fluorescence, and cells exhibiting fluorescence below 1.1 log were considered dextran-negative (N), cells exhibiting fluorescence above 1.1 log were considered dextran-positive, and were divided into cells exhibiting low fluorescence (L, 1.1 to 2.05 log) or high fluorescence (H, 2.05 to 3.7 log). Data are histograms of dot plots (50,000 cells per each sample) from a representative experiment with one BLV-positive cow. The cell numbers are relative and not comparable between histograms, because the individual histograms were scaled independently.
Figure 8:
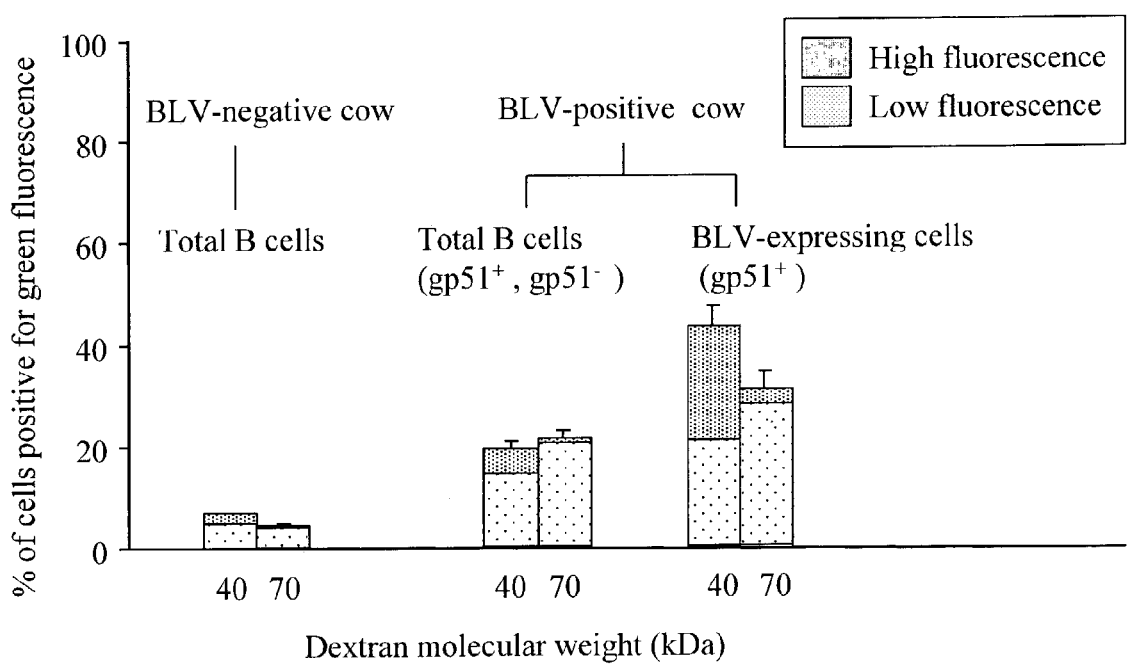
FIG. 8 shows the permeability of B lymphocytes from BLV-negative and BLV-positive cattle. PBMC from BLV-negative or BLV-positive cattle were incubated for one h with 40 kDa or 70 kDa fluorescein-conjugated dextrans (green fluorescence) and analyzed by flow cytometry. Lymphocyte subpopulations were identified in separate samples on the basis of staining with Tri-Color labeled monoclonal antibodies (red fluorescence) as B cells (positive for CD21-like antigen), and as BLV-expressing cells (positive for viral gp51 antigen), and assessed for dextran content by green fluorescence. Cells exhibiting fluorescence above 1.1 log were considered dextran-positive, and were divided into cells exhibiting low fluorescence (1.1 to 2.05 log) and high fluorescence (2.05 log to 3.7 log). Results are percentages of cells in each category exhibiting green fluorescence+SE. Data are from a representative experiment performed in triplicate.

Although binding of radiolabelled Stx to bovine blood cells or to free virus was not detected, flow cytometric analysis showed that the numbers of BLV-expressing cells were specifically reduced in cultures treated with Stx, as described in EXAMPLE 5. BLV-expressing cells from BLV-positive cattle were highly permeable to 40 and 70 kDa fluorescent dextrans (see Table 2; FIGS. 7 and 8), indicating that direct absorption of toxins by virus-expressing cells is a potential mechanisms for the antiviral activity of Shiga-toxins.

Additional details of this aspect of the invention are described in EXAMPLES 1, 4, and 5. A sequence coding for a Shiga-toxin polypeptide of the present invention can be inserted ex vivo into cells previously removed from a given animal. Such transformed autologous or homologous host cells, reintroduced into the animal or human, will express directly the corresponding Shiga-toxin polypeptide in vivo. The feasibility of such a therapeutic strategy to deliver a therapeutic amount of an agent in close proximity to the desired target cells and pathogens (e.g., to the virus, more particularly to the retrovirus, specifically to HIV and its envelope glycoprotein gp120), has been demonstrated in studies with cells engineered ex vivo to express sCD4 (Morgan et al. (1994) AIDS Res. Hum. Retroviruses 10: 1507–15).

The present invention also provides methods and compositions for suppressing BLV-related lymphocyte proliferation by administering a Shiga-toxin polypeptide to a ruminant. BLV infections in cattle are chronic and, in most animals, the disease does not progress to the malignant stage. Although antibodies to BLV are clearly important in viral repression (Portetelle et al. (1980) Virology 105(1): 223–33; Bruck et al. (1994) Virology 136(1):20–31), they do not always prevent progression of BLV infection to the PL and malignant stages. Consequently, other factors interfering with BLV replication may play a role in a suppression of this virus. The effect of Stx1 on SLP provides strong support for the premise that Shiga-toxin polypeptides serve a protective role in BLV-infected cows. Gastrointestinal Shiga-toxin producing Escherichia coli (STEC) release toxin systemically because cattle have anti-Stx antibodies in serum and colostrum (Pirro et al. (1995) Vets. Microbiol. 43(2–3): 131–41). More evidence to support the movement of the toxin out of the gastrointestinal tract comes from tissue culture experiments. Biologically active Stx1 is capable of moving across a monolayer of the intact polarized human intestinal epithelial cells (Acheson et al. (1996) Infect. Immun. 64:3294–3300). Therefore, Stx1 administered to ruminants in their feed should be capable of crossing the intestine. Stx1 is not cytotoxic to normal bovine PBMC (Menge et al. (1999) Infect. Immun. 67(5):2209–17) and, consequently, the presence of Stx in tissues or body fluids of cattle harboring BLV could benefit these animals, for example, by causing deletion of the BLV-expressing cells, by inhibiting viral expression and propagation, or by inhibiting the transmission of BLV between animals.

Thus, in another embodiment, the invention provides a method for treating a BLV-related disorder in a ruminant. In the method, an amount of a Shiga-toxin composition effective to suppress BLV-related cell proliferation is administered to the ruminant. The BLV-related disorder can include persistent lymphocytosis, malignant lymphoma, and the progression of viral infection.

As noted above, in another aspect, the invention provides Shiga-toxin compositions. In one embodiment, the composition includes an amount of a Shiga-toxin polypeptide effective to suppress BLV-related lymphocyte proliferation in an animal subject when administered to the animal. The composition can further include an acceptable carrier.

In addition to partially and fully purified Shiga-toxin polypeptides, the compositions of the invention include a probiotic microorganism that has been modified to express a Shiga-toxin polypeptide having antiviral activity. Any expression vector containing replicon and control sequences that are derived from species compatible with the host cell may be used in the practice of the invention. The term "expression vector" refers to a piece of DNA, usually double-stranded, which may have inserted into it a piece of heterologous DNA. The vector or replicon may be, for example, of plasmid or viral origin. Vectors contain sequences that facilitate the autonomous replication of the vector in a host cell. The term "replicon" in the context of this disclosure also includes sequence regions that target or otherwise facilitate the recombination of vector sequences into a host chromosome. The vector is used to transport the heterologous DNA into a suitable host cell. Heterologous DNA is defined as DNA not naturally found in the host cell. In the context of the present invention, heterologous DNA includes coding sequences for Shiga-toxin polypeptides and selectable markers used to screen for successful introduction of the expression vector into the host cell. Once in the host cell, the expression vector can replicate independently of, or coincidental with, the host chromosomal DNA, and several copies of the vector including the heterologous DNA may be generated. Alternatively, the expression vector may target the insertion of the heterologous DNA into a host chromosome. In addition, the vector also contains the necessary elements that permit transcription of the heterologous DNA into a mRNA molecule or otherwise cause replication of the heterologous DNA into multiple copies of RNA. Some expression vectors additionally contain sequence elements adjacent to the inserted foreign DNA that allow translation of the mRNA into a protein molecule. Many molecules of the mRNA and polypeptide encoded by the heterologous DNA can thus be rapidly synthesized.

The terms "transformation" and "transformed cell" refer to the introduction of DNA into a cell. The vector usually has a replication site, marker genes that provide phenotypic selection in transformed cells, one or more promoters, and a polylinker region containing several restriction sites for insertion of foreign DNA. Plasmids typically used for transformation of *E. coli* include pBR322, pUC18, pUC19, pUCI18, pUC119, and Bluescript M13, all of which have been described (Sambrooketal. (1989) *Molecular Cloning—A Laboratory Manual*, Cold Spring Harbor Laboratory, Cold Spring Harbor, N.Y.). However, many other suitable vectors are available as well. These vectors contain genes coding for ampicillin and/or tetracycline resistance which enables cells transformed with these vectors to grow in the presence of these antibiotics.

The promoters most commonly used to achieve expression in prokaryotic vectors include the β-lactamase (penicillinase) and lactose promoter systems (Itakura et al. (1977) *Science* 198:1056; Chang et al. (1978) *Nature* 375:617–24; Goeddel et al. (1979) *Nature* 281:544–48) and a tryptophan (trp) promoter system (Goeddel et al. (1980) *Nucl. Acids Res.* 8:4057), and the alkaline phosphatase systems. While these are the most commonly used, other microbial promoters have been utilized, and details concerning their nucleotide sequences have been published, enabling a skilled worker to ligate them functionally into plasmid vectors (see Siebenlist et al. (1980) *Cell* 20:269–91). Prokaryotic host cells or other host cells with rigid cell walls are preferably transformed using the calcium chloride method (Sambrook et al. (1989) *Molecular Cloning—A Laboratory Manual*, Cold Spring Harbor Laboratory, Cold Spring Harbor, N.Y.). Alternatively, electroporation may be used for transformation of these cells. Several techniques for the transformation of prokaryotes can be used (Hanahan et al. (1991) *Meth. Enxymol.* 204:63–113).

A representative method for expressing Stx1A in a probiotic microorganism is described in EXAMPLE 2. Those skilled in the art will recognize that various modifications can be made to the methods and genes described herein while not departing from the spirit and scope of the present invention. For example, in order to circumvent the potential cytotoxicity of cytoplasmic accumulation of a Shiga-toxin polypeptide, probiotic microorganisms may be manipulated to secrete these polypeptides.

In another embodiment, the present invention provides a naturally-occurring probiotic microorganism that expresses a Shiga-toxin having antiviral activity and that has been modified to eliminate expression of the B subunit of the holotoxin. One skilled in the art will recognize various approaches for deleting the B subunit from the microorganism, for example, by using homologous recombination as described in Schulz et al. (1997) *J. Clin. Invest.* 100: 1590–95.

In a further embodiment, the invention provides a transgenic plant that has been modified to express a Shiga-toxin polypeptide having antiviral activity. Suitable plants include tobacco and *Chenopodium quinoa*, among others. The genetic information required for expression of a Shiga-toxin polypeptide having antiviral activity is introduced into plants using a plant expression vector, which contains the necessary elements to stably integrate a gene to be expressed in plants and passed on to its progeny. As used herein, the term "gene" refers to an element or combination of elements that are capable of being expressed in a cell, either alone or in combination with other elements. In general, a gene comprises (from the 5' to the 3' end): (1) a promoter region, which includes a 5' nontranslated leader sequence capable of functioning in plant cells; (2) a gene or DNA sequence, which codes for the desired protein; and (3) a 3' nontranslated region, which typically causes the termination of transcription and the polyadenylation of the 3' region of the RNA sequence. Each of these elements is operably linked by sequential attachment to the adjacent element. A gene comprising the above elements may be inserted by standard recombinant DNA methods into a plant expression vector.

The segment of DNA referred to as the promoter is responsible for the regulation of the transcription of DNA into mRNA. A number of promoters which function in plant cells are known in the art, and may be employed in the practice of the present invention. These promoters may be obtained from a variety of sources such as plants or plant viruses, and may include, but are not limited to, promoters isolated from the caulimovirus group such as the cauliflower mosaic virus 35S promoter (CaMV35S), the enhanced cauliflower mosaic virus 35S promoter (CaMV35S), the figwort mosaic virus full-length transcript promoter (FMV35S), and the promoter isolated from the chlorophyll a/b binding protein. The nontranslated leader sequence can be derived from any suitable source and can be specifically modified to increase the translation of the mRNA. The 5' nontranslated region can be obtained from the promoter selected to express the gene, the native leader sequence of the gene or coding region to be expressed, viral RNAs, suitable eucaryotic genes, or a synthetic gene sequence. The termination region or 3' nontranslated region is employed to cause the termination of transcription and the addition of polyadenylated ribonucleotides to the 3' end of the transcribed mRNA sequence. The termination region may be native with the promoter region, native with the gene, or may be derived from another source, and would preferably include a terminator and a sequence coding for polyadenylation. Suitable 3' nontranslated regions of the chimeric plant gene include, but are not limited to: (1) the 3' transcribed, nontranslated regions containing the polyadenylation signal of *Agrobacterium* tumor-inducing (Ti) plasmid genes, such as the nopaline synthase (NOS) gene, and (2) plant genes like the soybean 7S storage protein genes and the pea small subunit of the ribulose 1,5-bisphosphate carboxylase-oxygenase.

The addition of appropriate introns and/or modifications of coding sequences for increased translation can also substantially improve transgene expression. Appropriate introns can include but are not limited to the maize hsp70 intron, maize adh 1 intron, and rice actin intron. Therefore, to select a vector for expression of a Shiga-toxin polypeptide, constructs containing various combinations of promoters and expression enhancement elements can be introduced into plant cells.

The most common method of plant transformation is performed by cloning a target transgene into a plant transformation vector that is then transformed into *Agrobacterium tumifaciens* containing a helper Ti-plasmid (Hoeckema et al. (1983) *Nature* 303:179–181). The *Agrobacterium* cells containing the expression vector are incubated with leaf slices of the plant to be transformed (Anetal. (1986) *Plant Physiol.* 81:301–305; see also Hooykaas (1989) *Plant Mol. Biol.* 13:327–36). Transformation of cultured plant host cells is normally accomplished through *Agrobacterium tumifaciens*. Cultures of host cells that do not have rigid cell membrane barriers are usually transformed using the calcium phosphate method or other methods for introducing DNA into cells such as Polybrene, protoplast fusion, electroporation, and direct microinjection into nuclei.

In addition to the methods described above, a large number of methods are known in the art for transferring cloned DNA into a wide variety of plant species, including gymnosperms, angiosperms, monocots and dicots. Plant transformation strategies and techniques are reviewed in Birch (1997) *Ann. Rev. Plant Phys Plant. Mol. Biol.* 48:297 and Forester (1997) *Exp. Agric.* 33:15–33. Minor variations make these technologies applicable to a broad range of plant species. In the case monocot transformation, particle bombardment appears to be the method of choice for most commercial and university laboratories. However, monocots such as maize can also be transformed by using *Agrobacterium* transformation methods as described in U.S. Pat. No. 5,591,616. The use of whiskers for the transformation of plant cells, particularly maize, is described in U.S. Pat. No. 5,464,765. Methods of transforming and regenerating soybean are described in U.S. Pat. No. 5,968,830. U.S. Pat. No. 5,969,215 describes transformation techniques for producing transformed *Beta vulgaris* plants, such as the sugar beet.

Each of the above transformation techniques has advantages and disadvantages. In each of the techniques, DNA from a plasmid is genetically engineered such that it contains not only the gene of interest, but also selectable and screenable marker genes, for example, the kan gene encoding resistance to kanamycin. A selectable marker gene is used to select only those cells that have integrated copies of the plasmid (the construction is such that the gene of interest and the selectable and screenable genes are transferred as a unit). The screenable gene provides another check for the successful culturing of only those cells carrying the genes of interest. Transformed plant calli may be selected through the selectable marker by growing the cells on a medium containing, for example, kanamycin, and appropriate amounts of phytohormone such as naphthalene acetic acid and benzyladenine for callus and shoot induction. The plant cells may then be regenerated and the resulting plants transferred to soil using techniques well known to those skilled in the art.

Traditional *Agrobacterium* transformation with antibiotic resistance selectable markers is problematical because of public opposition that such plants pose an undue risk of spreading antibiotic tolerance to animals and humans. Such antibiotic markers can be eliminated from plants by transforming plants using the *Agrobacterium* techniques similar to those described in U.S. Pat. No. 5,731,179. Antibiotic resistance issues can also be effectively avoided by the use of bar or pat coding sequences, such as is described in U.S. Pat. No. 5,712,135. These preferred marker DNAs encode second proteins or polypeptides inhibiting or neutralizing the action of glutamine synthetase inhibitor herbicides phosphinothricin (glufosinate) and glufosinate ammonium salt.

There are numerous factors which influence the success of transformation. The design and construction of the expression vector influence the integration of the heterologous sequence into the chromosomal DNA of the plant nucleus and the ability of the transgene to be expressed by the cell. A suitable method for introducing the expression vector into the plant cell nucleus in a nonlethal manner is preferred. Importantly, the type of cell into which the construct is introduced must, if whole plants are to be recovered, be of a type which is amenable to regeneration, given an appropriate regeneration protocol. A representative method for preparing a transgenic plant expressing a Shiga-toxin polypeptide is described in EXAMPLE 3.

A transgenic plant of the present invention expressing a Shiga-toxin polypeptide having antiviral activity can be cultivated using methods known to those of ordinary skill in the art. The presence of a Shiga-toxin gene, or gene product, in the transformed plant may be determined by any suitable method known to those skilled in the art. Included in these methods are Southern, northern, and western blot techniques, ELISA, and bioassays. A representative assay for determining the presence of a Shiga-toxin gene or gene product in the transformed plant is described in EXAMPLE 3.

The transgenic plants of the present invention can be further propagated to generate genetically true-breeding populations of plants possessing the modulated cell division trait. Further, the transgenic plants can be crossed with other plant varieties, having one or more desirable phenotypic traits, such as, for example, stress and pest resistance or nutritional and taste quality, to generate novel plants possessing the aforementioned desirable traits in combination with the transgenic trait that modulates cell division.

In one embodiment of the method of the invention, a composition including a Shiga-toxin polypeptide having antiviral activity is administered to a ruminant in an amount effective to eliminate BLV-infected cells and/or to prevent the expression and propagation of BLV. Shiga-toxin polypeptides that are nontoxic to humans and other animals, such as Stx1A, are preferred.

There are several ways in which a Shiga-toxin polypeptide can be administered to a ruminant. For example, a Shiga-toxin composition can be administered in a variety of ways including oral, rectal, intranasal and intravenous. The composition containing the Shiga-toxin polypeptides can be in any form suitable for the intended method of administration, including, for example, a solution, a suspension, or an emulsion. The composition can also be administered as an admixture with a suitable carrier or diluent. Such an admixture can be prepared according to conventional compounding techniques. The carrier may take a wide variety of forms depending on the form of preparation desired for administration. Suitable carriers include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinyl-pyrrolidinone, low melting waxes, ion exchange resins, and the like, as well as combinations of any two or more thereof.

Liquid carriers are typically used in preparing solutions, suspensions, and emulsions. Liquid carriers for use in the practice of the present invention include, for example, water, saline, acceptable organic solvent(s), acceptable oils or fats, and the like, as well as mixtures of two or more thereof. The liquid carrier can contain other suitable additives such as solubilizers, emulsifiers, nutrients, buffers, preservatives, suspending agents, thickening agents, viscosity regulators, stabilizers, and the like.

Compositions of the present invention can also be in the form of microparticles, microcapsules, liposomal encapsulates, and the like, as well as combinations of any two or more thereof. Solid dosage forms for oral administration can include capsules, tablets, pills, powders, and granules. In such solid dosage forms, the Shiga-toxin composition may be admixed with at least one inert diluent such as sucrose, lactose, or starch. Such dosage forms may also comprise additional substances other than inert diluents, for example, lubricating agents such as magnesium stearate. In the case of pills, capsules, and tablets, the dosage forms can also comprise buffering agents. Tablets and pills can be prepared with enteric coatings.

The Shiga-toxin compositions of the present invention are administered in a therapeutically effective dose. A therapeutically effective dose can be determined by a variety of methods. For example, an effective dose can be determined by in vitro experiment followed by in vivo studies. The amount of Shiga-toxin composition that can be combined with a carrier to produce a single dosage form will vary depending upon the specific composition, the animal treated, and the administration mode. The specific dose level for any particular animal will depend upon a variety of factors including the antiviral activity of the composition employed, the age, body weight, general health, sex, diet, time of administration, administration route, excretion rate, and the severity of the BLV-related disease in the animal.

In one embodiment of the invention, the Shiga-toxin polypeptide is delivered to the ruminant in a purified or partially purified form. A representative method for Shiga-toxin polypeptide purification is described in EXAMPLE 1. There are a variety of modes of administration of pure or partially purified composition of a Shiga-toxin polypeptide to a ruminant. Suitable modes of administration include enteral, intramuscular, transmucosal, intravenous, intranasal, rectal, and the like.

In another embodiment of the invention, the Shiga-toxin polypeptide can be delivered to the ruminant through the administration of a probiotic microorganism that, produces a Shiga-toxin polypeptide. There are a variety of probiotic microorganisms suitable for use in this invention including *E. coli, Aeromonas*, and *Citrobacter*. It will be appreciated that other suitable microorganisms that are harmless to ruminants can be used.

In the method of the invention, a Shiga-toxin composition is administered to suppress BLV-related lymphocyte proliferation. In one embodiment, the administered composition includes a naturally occurring probiotic microorganism that expresses a Shiga-toxin polypeptide. Suitable microorganisms can include *E. coli*. For example, there are more than 100 serotypes of *E. coli* that produce Shiga-toxin, most of which have been shown not to be human pathogens. In another embodiment, the composition includes a probiotic microorganism that expresses a Shiga-toxin that has been modified to eliminate expression of the B subunit of the holotoxin. In a further embodiment, a Shiga-toxin polypeptide is provided in the form of a probiotic organism that has been genetically modified to express the polypeptide.

Administration of a probiotic microorganism can be accomplished by any suitable method for introducing the organism into the digestive tract. The microorganism can be mixed with a carrier and applied to liquid or solid feed or to drinking water. The carrier is preferably nontoxic to the microorganism and the animal. Preferably, the carrier includes one or more ingredients that promote the viability of the microorganism during storage. The microorganism can also be formulated as an inoculant paste to be directly injected into an animal's mouth. The formulation can include other ingredients to improve palatability, improve shelf-life, impart nutritional benefits, and the like. If a reproducible and measured dose is desired, the microorganism can be administered by a rumen cannula, as described in U.S. Pat. No. 5,965,128. The amount of probiotic microorganism to be administered is governed by factors affecting efficacy.

In another embodiment of the invention, a Shiga-toxin polypeptide having antiviral activity can be delivered to the ruminant in the form of a transgenic plant expressing a Shiga-toxin polypeptide. Administration of a transgenic plant expressing a Shiga-toxin polypeptide can be accomplished by any suitable method for introducing the plant into the digestive tract. For example, the transgenic plant, or part thereof, can be administered in a fresh or dried form. The transgenic plant can also be mixed with a carrier and applied to liquid or solid feed or to drinking water. The carrier material is preferably nontoxic to the plant and the animal. Preferably, the carrier contains one or more ingredients that promote the preservation of the Shiga-toxin polypeptide during storage. Plant material can also be formulated as an inoculant paste to be directly injected into an animal's mouth. The formulation can include other ingredients to improve palatability, improve shelf-life, impart nutritional benefits, and the like.

The following examples are provided for the purposes of illustrating, and not limiting, the present invention.

EXAMPLES

Example 1

Suppression of Bovine Leukemia Virus Spontaneous Lymphocyte Proliferation by Stx1

In this example, the suppression of BLV-related spontaneous lymphocyte proliferation by administering purified Stx1 holotoxin and Stx1 subunit A is described.

Materials and Methods. Freisian-Holstein cows from the University of Idaho dairy were used as blood donors. Cows were identified as BLV-positive by high titers of anti-BLV antibody. Five persistently lymphocytotic (PL) cows were identified by elevated numbers and percentages of B cells (three standard deviations above normal levels) in peripheral circulation and used as BLV-positive donors. Cows with no detectable anti-BLV antibodies were used as BLV-negative donors.

Blood was collected by jugular venipuncture into acid-citrate-dextrose (ACD) (one part to four parts whole blood). PBMC were purified by density gradient centrifugation using Accu-Paque (Accurate Chemical and Scientific Corp., Westbury, N.Y.) (1.086 g/ml) as previously described (Ferens et al. (1998) *Infect Immun.* 66(2):573–80). Erythrocytes were lysed by incubation in warm ammonium chloride, and PBMC preparation was washed several times in PBS/ACD mix (4:1) to remove platelets. PBMC were cultured in 96-well culture plates (Coming) at the initial density of $2.5 \times 10^6$ cells/ml ($0.5 \times 10^6$ cells/well) in RPMI-1640 with 20% heat-inactivated fetal bovine serum, 2 mM L-glutamine, 100 units/ml penicillin and 100 µg/ml streptomycin. To assay cell proliferation, 3H-thymidine was added to the wells (1.0 µCi/well) 48 hr after the start of cell culture and 16–18 hr prior to cell harvest. Cells were harvested on a semiautomated 96-well plate harvester (Skatron Inc., Sterling, Va.) and the amount of 3H-thymidine incorporated was determined by liquid scintillation spectroscopy (Packard Instrument Co., Downers Grove, Ill.) and expressed as counts per minute (CPM). In all experiments measurements were obtained in at least four replicate samples. The percentage inhibition of proliferation was expressed as (CPM of cultures with toxin/CPM of control cultures without toxin)×100.

Recombinant Shiga toxin 1 (Stx1) A and B subunits were purified as previously described (Zollman et al. (1994) *Prot. Expr. Purif* 5:291–295; Austin & Hovde (1995) *Prot. Expr. Purif* 6:771–779). Briefly, Stx1A was purified from *E. coli* SY327(pSC25). Concentrated periplasmic proteins were adsorbed to Matrex Gel Green A agarose (Amicon) equilibrated with 10 mM PBS and Stx1A eluted as a single protein peak with approximately 0.3 M NaCl in a 0.15–1.0 M NaCl gradient. Stx1B was purified from *E. coli* JM105(pSBC32). Periplasmic proteins were fractionated by ammonium sulfate precipitation and Stx1B was separated by isoelectric focusing and native polyacrylamide gel electrophoresis. Holotoxin was reconstituted in vitro by combining Stx1A and Stx1B in 1:10 molar in 10 mM Tris HCl (pH 7.0) and dialyzed against 10 mM Tris-HCl (pH 7.0). The association of A and B subunits was confirmed by immunoblot of proteins separated by analytical discontinuous native-polyacrylamide gel electrophoresis. Before use in cultures, toxins were dialyzed exhaustively against 10 mM PBS and concentrations were measured using a Bio-Rad assay with bovine albumin as a standard.

To measure BLV expression, PBMC suspended at the initial density of $2.5 \times 10^6$ cells/ml were placed in culture dishes (4.0 ml per dish) without toxin or with 1.0 µg/ml Stx1 A. The cells were harvested at 12, 18, 24, 48, and 72 hr; centrifuged, and resuspended in 0.5 ml of 0.1 M Tris buffer (pH 7.5) with 0.1 M ethylenediaminetetraacetic acid and 0.1 M phenylmethylsulfonyl fluoride. Samples were subjected to repeated freeze-thaw cycles until cells were lysed, as determined microscopically. Supernatant was transferred to nitrocellulose using a 96-well blotter, and cell lysates were probed with the murine monoclonal antibody BLV-3 against the BLV 24 kDa protein referred to throughout as anti-p24, and antimouse antibody conjugated to alkaline phosphatase (Sigma, St. Louis, Mo.). Immunoblots were developed using 5-bromo-4-chloro-3-indolyl phosphate (BCIP) and nitro blue tetrazolium (Sigma, St. Louis, Mo.) as substrate, according to manufacturer's instruction, scanned using Hewlett-Packard densitometer, and the results were quantitated using Molecular Analyzer analytical program. The cultures of BLV-negative PBMC served as negative controls.

Concanavalin A (ConA) and pokeweed mitogen (PWM) were purchased from Sigma (St. Louis, Mo.). Human recombinant interleukin-2 (IL-2) was purchased from Gibco, BRL (Grand Island, N.Y.). Polyclonal antibody to Stx1A was generated by standard technique in New Zealand white rabbits. Lipopolysaccharide (LPS) of *Salmonella typhimurium* was purchased from DIFCO Laboratories (Detroit, Mich.). Murine monoclonal antibodies BLV-1 against the 51 kDa glycoprotein of BLV (referred to throughout as antigp51), and control antibody COLIS69A of the same isotype (IgGl) were purchased from WSU Monoclonal Antibody Center (Pullman, Wash.).

The results are presented as arithmetic means±standard errors (SE). In all experiments measurements were made from four or more replicates. Unless otherwise stated, the results are means of three or more experiments. Analysis of variance (ANOVA) was used to establish statistical significance at $p \leq 0.05$.

Stx1 suppresses SLP in cultures of PBMC from BLV-infected cows. PBMC from five BLV-positive cows in the persistently lymphocytotic stage of infection invariably proliferated in vitro, and this SLP was consistently suppressed by Stx1 (FIG. 1). Holotoxin or the A subunit alone (Stx1A) were potent suppressors of SLP, acting in a dose-dependent manner over the range of concentrations tested. The effects of Stx1A or holotoxin were significantly different at 0.1 and 0.5 µg/ml because the 95% confidence intervals of the percent proliferation values did not overlap. Compared to Stx1A, the B subunit (Stx1B) was far less potent in suppressing SLP even with molar concentrations of Stx1B more than 4-fold higher than Stx1A. Moreover, in contrast to Stx1A, Stx1B did not act in a dose-dependent fashion. The 95% confidence intervals of the percent proliferation values were overlapping for all concentrations of Stx1B.

Cellular proliferation in spontaneously proliferating cultures of BLV-positive PBMC almost exclusively involves B lymphocytes (Esteban et al. (1985) *Cancer Res.* 45(7):3225–30; Jensen et al. (1990) *Vet. Immunol. Immunopathol.* 26(4):333; Mirsky et al. (1996) *J. Virol.* 70(4):2178–83). Thus, to evaluate Stx1 activity on normal B cells, Stx1 inhibition of poke weed mitogen (PWM)-induced proliferation of normal BLV-free PBMC was measured because PWM primarily stimulates B cells. In contrast to SLP, PWM-induced proliferation of BLV-free PBMC was only weakly sensitive to Stx1 (FIG. 1). Low doses of Stx1A or Stx1 (0.1 µg/ml), sufficient to reduce SLP by 45% and 60%, respectively, caused <10% inhibition of proliferation induced by PWM. Stx1A at the highest concentration tested inhibited the PWM-induced proliferation by only 30%, whereas Stx1B or holotoxin were either marginally inhibitory or had a weak-stimulatory effect in cultures from some donors.

To determine whether bovine T lymphocytes constitute targets for Stx1, the impact of Stx1 on PBMC proliferation induced by Concanavalin A (ConA) was tested. ConA is a lectin that induces T-cell proliferation by specific interaction with the T-cell receptor complex. T-cell proliferation induced by ConA was not affected by Stx1 holotoxin or toxin subunits.

These results indicate that SLP of BLV-positive PBMC is susceptible to Stx1-mediated inhibition, and that the inhibitory effect is mediated by the A subunit of holotoxin. Subsequent experiments to further characterize toxin activity were performed with purified Stx1A or B subunits.

BLV positive PBMC treated with Stx1A retain responsiveness to immunostimulation. To assess whether the toxin was selectively targeting SLP or indiscriminately suppressing the ability of BLV-positive PBMC to respond to immunostimulation, the impact of Stx1A on cellular proliferation was tested in cultures of BLV-positive PBMC supplemented with IL-2, a potent B-cell activator. The addition of 1.0 ng/ml of IL-2 to BLV-positive cultures strongly augmented proliferation, evidenced by a gain of about $6.0 \times 10^4$ CPM-per well (Table 1). This IL-2-induced proliferation was preserved even in the presence of 1.0 μg/ml of Stx1A, a toxin concentration sufficient to cause almost complete suppression of SLP. Moreover, proliferation in these cultures exceeded proliferation in cultures of BLV-negative PBMC treated with combination of Stx1A and IL-2 (Table 1).

TABLE 1

The effect of Stx1A and IL-2 on the Proliferation of BLV-positive and BLV-negative PBMC.

| PBMC | Stx1A[a] | IL-2 0 | 0.1 ng/ml | 1.0 ng/ml |
|---|---|---|---|---|
| BLV-Positive | 0 | 77.3 ± 4.8[b] | 97.3 ± 3.2 | 136 ± 1.5 |
| | 0.1 μg/ml | 38.3 ± 1.3 | 60.5 ± 1.9 | 123 ± 1.1 |
| | 1.0 μg/ml | 10.0 ± 0.8 | 22.1 ± 0.2 | 61.5 ± 2.2 |
| BLV-Negative | 0 | 0.7 ± 0.04 | 6.8 ± 0.6 | 42.5 ± 0.3 |
| | 0.1 μg/ml | 0.5 ± 0.1 | 6.8 ± 0.7 | 34.1 ± 0.5 |
| | 1.0 μg/ml | 1.0 ± 0.2 | 5.7 ± 0.2 | 25.9 ± 1.1 |

[a]toxin and IL-2 were added at the start of the cell culture
[b]mean CPM × $10^{-3}$ ± SE of four measurements from a typical experiment.

BLV-positive cultures treated with Stx1A also retained the ability to respond to stimulation with PWM. These results indicate that inhibition of SLP by Stx1 involves selective action on a sub-population of PBMC and does not alter the ability of B cells not targeted by the toxin to respond to immunostimulation. Additional support for the premise that Stx1 targets a selected and probably minor subpopulation of B cells comes from the finding that cell death, detected by trypan blue inclusion or cell shrinkage measured by flow cytometry, was not increased in cultures treated with Stx1A. This finding is consistent with the fact that although the majority of B-cells from cows in PL stage contain provirus, very few PBMC from BLV-positive cattle express viral proteins (Baliga & Ferrer (1977) *Proc. Soc. Exp. Biol. Med.* 156(2):388–91; Gupta et al. (1984) *J. Virol.* 50(1).267–70; Chatterjee et al. (1985) *J. Virol.* 54(3):860–3; Levy et al. (1987) *Leukemia* 1(5):463–5).

The impact of Stx1A on PBMC cultures stimulated with lipopolysaccharide (LPS) was also examined. This gram-negative bacteria cell wall component can significantly influence immune responses, and was shown to stimulate BLV expression in cultures of BLV-positive PBMC (Kidd & Radke (1996) *Virology* 217(1):167–77). LPS used at concentration of 0.1 μg/ml increased proliferation of BLV-positive PBMC twofold but did not induce normal PBMC cultures to proliferate, indicating that only BLV-positive cultures were susceptible to mitogenic stimulation by low concentrations of LPS. The increased proliferation resulting from LPS application was completely abrogated by treatment with Stx1A, further indicating that cells involved in SLP constitute the cellular targets of Stx1A.

Figure 2:
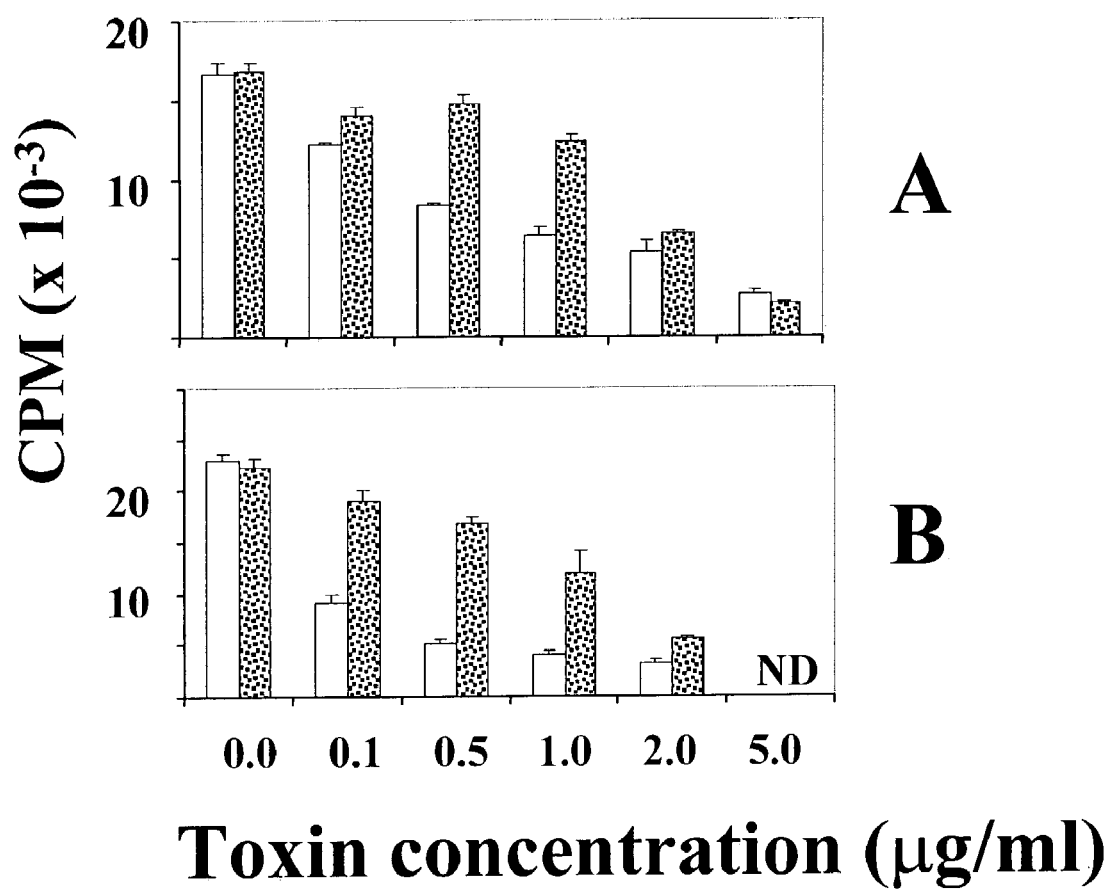
FIGS. 2A and 2B illustrate the effect of antitoxin on Stx1-mediated inhibition of SLP in PBMC cultures from persistently lymphocytotic (BLV-positive) cows. PBMC from BLV-positive cows were incubated with varying concentrations of toxin (A, A subunit; B, holotoxin,) without anti-Stx1A (open bars) and with anti-Stx1A diluted 1:100 (stippled bars). Cell proliferation was measured as incorporation of tritiated thymidine and expressed as counts per minute (CPM). Data are means±SE from four replicates from a representative experiment. ND refers to not done.

Anti-Stx1A serum prevents inhibition of SLP by Stx1. To determine if a spurious inhibitor was present in the toxin preparations, the ability of anti-Stx1A immune serum to neutralized Stx1 or Stx1A suppression of SLP was tested. Antitoxin neutralized Stx1 or Stx1A activity in a dose-dependent manner (FIG. 2) and did not affect cellular proliferation in cultures without toxin. The antitoxin was effective within a range of titers from 1:1000 to 1:50, but did not have a neutralizing ability outside this range. Within this range the ability of antitoxin to neutralize increasingly greater doses of Stx1A was directly proportional to concentration. For example, antitoxin restored about 80% to >50% of the thymidine incorporation in BLV-positive cultures treated with up to 1.0 μg/ml Stx1A or Stx1, respectively (FIG. 2). A two-way ANOVA indicated statistically significant differences among the effects of various concentrations of toxin and antitoxin as well as a significant interaction of these two factors.

Inhibition of SLP by antiviral antibody or Stx1A is similarly time-dependent. SLP in cultures of BLV-positive PBMC is preceded within 24 hr of culture by de novo synthesis of viral proteins and dissemination of viral particles (Baliga & Ferrer (1977) *Proc. Soc. Exp. Biol. Med.* 156(2):388–91). It is known that anti-BLV serum can block SLP (Trueblood et al. (1998) *J. Virol.* 72(4):3169–77). To assess whether viral proteins accessible to antibody were required to sustain SLP, the ability of antiviral antibody to interfere with SLP over a two-day period was examined. Monoclonal anti-gp51 was able to reduce thymidine incorporation in spontaneously proliferating cultures by 60% (FIG. 3). However, this inhibition required application of anti-gp51 at the beginning of cell culture (FIG. 3). Inhibition of SLP by anti-gp51 was due to a specific interaction with viral proteins, because this antibody did not affect IL-2-induced proliferation of BLV-negative PBMC, and control monoclonal antibody of the same isotype had no effect on SLP. These results are in agreement with the findings that dissemination of BLV proteins is involved in initiation of SLP, but they also suggest that BLV proteins are not required for continuation of an established SLP event.

To determine if toxin also acts on SLP in a time-dependent fashion, Stx1A or Stx1B was administered to cultures of BLV-positive PBMC at various times after the start of cell culture. Similar to treatment with anti-gp51, the ability of Stx1A to inhibit SLP was reduced if cells were precultured in medium for 24 hours before toxin application (FIG. 3). Stx1A applied on day 2 of culture at concentrations of up to 1.0 μg/ml had only minimal impact upon SLP (FIG. 3) and even 5.0 μg/ml Stx1A applied on day 2 of culture reduced thymidine incorporation in spontaneously proliferating cultures by only 30 to 40%. These results suggest that inhibition of SLP by Stx1A is time-dependent, and may be based on the ability of the toxin to interfere with the initiation of spontaneous proliferation. The fact that susceptibility of SLP to inhibition by either Stx1A or anti-gp51 lessens within 24 hours of culture evidences that the cells involved in dissemination of viral proteins and the initiation of SLP constitute targets for Stx1.

In contrast to Stx1A, the relatively minor effect of Stx1B on SLP did not change when Stx1B was applied after a preculture without toxin. This difference suggests that Stx1B and Stx1A have different modes of action, and likely affect different subpopulations of PBMC.

Stx1A reduces expression of BLV core protein. To directly test antiviral activity of Stx1, the expression of BLV p24 core protein in PBMC cultured with or without Stx1A was assayed. Immunoblot analysis of cell lysates of PBMC cultured for 12 hr showed a reduction in the amount of p24 protein in cells treated with 1.0 µg/ml toxin compared to cells in the control cultures without toxin (FIG. 4). The optical density of the immunoreaction in the sample treated with toxin was 442-fold less than the immunoreaction in the sample without toxin, suggesting that toxin suppressed viral protein synthesis.

The results demonstrate the antiviral activity of Stx. The results are consistent with research showing antiviral activity of the RIP family of toxins (reviewed in Stirpe et al. (1992) *Bio-Technology* 10:405–412). The results also demonstrate that Stx1 is a potent suppressor of SLP and that this activity is mediated by the A subunit of Stx1. The most likely explanation for this result is that Stx1 has an adverse impact on the cells that express the virus. It is well established that SLP is preceded and accompanied by synthesis of viral proteins (Takashima & Olson (1981) *Arch Virol.* 69(2): 141–8; Kerkhofs et al. (1996) *J. Virol.* 70(4):2170–7). The premise that Stx1 has antiviral activity is supported by the fact that maximal SLP sensitivity to Stx1 was exhibited within the first 24 hours of culture. A similar time-dependent loss of sensitivity of SLP to antigp51-mediated inhibition was also found. Both these findings are consistent with the fact that the expression of BLV particles in culture reaches maximum after 12 to 24 hr of cell culture (Zandomeni et al. (1992) *J. Gen. Virol.* 73(8):1915–24). Inhibition of SLP by BLV-specific antibody is well established (Thorn et al. (1981) *Infect. Immun.* 34(1):84–9; Trueblood et al. (1998) *J. Virol.* 72(4):3169–77), and possibly results from the interference with the release of BLV particles from cultured cells (Driscoll et al. (1977) *Arch. Virol.* 55(1–2):139–44).

The reduced expression of BLV p24 protein in cell cultures treated with Stx1 could be due either to the nonlethal suppression of viral protein synthesis or Stx1-mediated lysis of the cells expressing viral proteins. The assay did not allow distinction between these possibilities because the determination of the p24 protein level was limited to the protein present within cells harvested from the cell cultures at a given time.

The suppression of SLP by Stx1 did not diminish the ability of B-cells in BLV-positive PBMC cultures to respond to immunostimulation by IL-2 or PWM. This implies that Stx1 suppresses SLP via a selective mechanism and is consistent with the fact that very few B cells in BLV-infected cattle express viral proteins or viral particles (Gupta et al. (1984) *J. Virol.* 50(1):267–70). Moreover, Stx1 had little effect on PWM-induced normal bovine B-cell proliferation and no adverse effect on ConA-induced bovine T-cell proliferation. These findings support the premise of a selective antiviral activity of Stx1. Especially relevant is the fact that Stx1 was a potent SLP inhibitor at low concentrations, which had only marginal impact on normal PBMC.

Similar to ricin, the archetype of the A:B RIPs, Stx1 holotoxin is composed of an enzymatically active A-chain and a cell-receptor binding B-chain pentamer. The A subunit alone was able to abrogate SLP and, compared to holotoxin, was similarly efficacious. Thus, sensitivity of target cells in BLV-positive culture to Stx1 occurs via a mechanism that does not require the B subunit. This is in a sharp contrast to the receptor-based mechanism by which Stx1 gains entry to Vero cells and other cellular targets described (Jackson (1990) *Microb. Pathogen.* 8:235–42; Bast et al. (1997) *Infect. Immun.* 65:2978–82). However, antiviral activity of the plant RIP proteins also does not require a B subunit. Class 1 RIPs composed solely of an enzymatic A chain are potent antiviral agents; examples include inhibition of HIV replication by pokeweed antiviral protein (Olson et al. (1991) *AIDS Res. Hum. Retroviruses* 7(12)1025–1030), bryodin (Wachinger et al. (1993) *Res. Exp. Med.* 193(1): 1–12), and trichosanthin (Byers et al. (1994) *AIDS Res. Hum. Retroviruses* 10(4):413–20). Similar anti-HIV activity is exhibited by an isolated A chain of ricin (Neukirch et al. (1981) *Arch Virol.* 69(3–4):287–90). Typically, inhibition of HIV-1 replication by plant RIP proteins occurs at the concentrations nontoxic to uninfected cells (Olson et al. (1991) *AIDS Res. Hum. Retroviruses* 7(12)1025–1030; Lee-Huang et al. (1995) *Proc. Natl. Acad. Sci. U.S.A.* 92(19):8818–22).

Inhibition of protein synthesis may not be the only mechanism of antiviral activity. Plant RIP proteins were shown to inhibit HIV-1 integrase via topological activity on long terminal repeats of viral DNA (Lee-Huang et al. (1995) *Proc. Natl. Acad. Sci. U.S.A.* 92(19):8818–22), and these proteins show structural similarities to retroviral reverse transcriptases (Ready et al. (1988) *Proteins* 3(1):53–9). Inhibition of HIV infection by plant RIPs involves regions of these proteins which are not required for ribosome inactivation, suggesting that the anti-HIV activity of ribosome-inactivating proteins may not be the result of N-glycosidase activity alone (Lee-Huang et al. (1994). *Proc. Natl. Acad. Sci. USA* 91(25):12208–12).

Interestingly, some antiviral activity of RIPs has been associated with the B subunit. For instance, ricin can agglutinate hog cholera virus (a small RNA virus) due to a galactose-binding ability of B subunit (Neukirch et al. (1981) *Arch Virol.* 69(3–4):287–90). Ricin was also able to agglutinate cells of a variety of leukemic cell lines, including NIH3T3 cells infected with Moloney leukemia virus (Koga et al. (1979) *Gann.* 70(5):585–91). These results agree with our finding that, although less efficaciously than Stx1A, Stx1B subunit was able to inhibit SLP to some degree. However, Stx1B-mediated inhibition of SLP was not time-sensitive, and was inferior to Stx1A at equivalent molar concentrations, further indicating that the mechanism of Stx1B action is different than that of Stx1A.

Example 2

Suppression of Bovine Leukemia Virus-Related Cell Proliferation by Administering to Cows a Probiotic *E. coli* Expressing Stx1A In this example, the suppression of BLV-related cell proliferation by administering a representative probiotic *E. coli* expressing Stx1A is described.

Materials and Methods. The techniques of amplification of genetic sequences with the polymerase chain reaction, cutting and splicing DNA into plasmids, transformation of bacteria with plasmids, and assays for antibody binding are all well known biotechnology methods and detailed descriptions of these methods can be found in a number of texts, for example Sambrook et al. (1989) Molecular Cloning-A Laboratory Manual, Cold Spring Harbor Laboratory, Cold Spring Harbor, N.Y.

Commonly used procaryotic control sequences, which are defined herein to include transcription initiation, optionally operator, and ribosome binding site sequences, can include commonly used promoters such as the beta-lactamase (penicillinase) and lactose (lac) promoter systems (Chang et al. (1978) Nature 375:617–24), the tryptophan (trp) promoter system (Goeddel et al. (1980) Nucl. Acids Res. 8:4057), and the lambda derived $P_L$ promoter and N-gene ribosome binding site (Shimatake et al. (1981) Nature 292:128). However, any available promoter system compatible with procaryotes can be used.

The successful expression attained by the invention depends upon correct utilization of the suitable control sequences to regulate expression of the desired toxin fragment. Therefore, control sequences compatible with and suitable for the host are positioned operably with respect to the coding sequence, using a properly placed "start" codon at the 5' end of the desired sequence. Any "native" control sequences are eliminated. The vectors of the invention place the coding sequence for Stx1A, immediately preceded by an ATG start codon directly downstream from control systems chosen to be compatible with the particular host.

It is also important, in obtaining good production of Stx1A, to regulate the "time" of production so as to minimize any lethal effect on the host cell. Most typically, even for procaryotes, this is done by delaying expression of the toxin sequences until substantial growth has occurred. Accordingly, it is desirable to utilize control sequences that are subject to environmental conditions. By maintaining conditions that repress expression during growth phase, and then converting to conditions which permit expression at the desired time, the negative aspects of any potentially lethal effect can be minimized. Inducible expression systems that have been used successfully to express ricin toxin, another class 2 RIP (see U.S. Pat. No. 6,084,073), are described below.

The trp promoter is a regulatable promoter where expression of the operably linked sequence can be controlled by the level of tryptophan in the medium. By maintaining high tryptophan levels during growth, expression is repressed. Depletion or competitive inhibition of tryptophan turns on the promoter and permits expression.

The $P_L$ promoter derived from lambda phage is regulated by a protein that can be temperature sensitive. Mutant forms of the wild type repressor, for example, $CI_{857}$, having this characteristic are known. When used in a host that is able to synthesize this mutant form of repressor, the $P_L$ promoter will be switched on when the temperature is raised because the higher temperature inactivates the mutant CI repressor. Thus, the host cells can be grown at low temperature without, or with, low production of the foreign protein. The temperature is then raised when growth has been attained and Stx1A production is desired.

When the phoA controlسequences are employed, expression can be delayed by maintaining the cells in the presence of phosphate ion and then depleting the phosphate levels when expression is desired.

A plasmid that has temperature sensitive copy number control may also be applied. If the cells are grown at low temperatures, coding sequences contained in the plasmid are replicated at low levels; at higher temperatures, the number of such copies is increased. The amount of protein produced is thus indirectly managed by regulating the number of available copies or its coding sequence.

Vector construction employs known ligation and restriction technique. A method for achieving intracellular expression of Shiga-toxin polypeptides in E. coli has been previously described (Zollman et al. (1994) Prot. Expr. Purif 5:291–295; Austin & Hovde (1995) Prot. Expr. Purif 6:771–779). Similar expression vectors and techniques, as well as others described above, can be used to direct expression of Shiga-toxin polypeptides in a probiotic E. coli. Any generic nonpathogenic bovine strain could be used, or a recA minus lab strain, for example strains E. coli 271 ATCC 202020, E. coli 786 ATCC 202018, and E. coli ATCC 202019 described in U.S. Pat. No. 5,965,128.

The expression vectors containing Stx1A coding sequences are transformed into the appropriate strains of E. coli and the cells grown under standard culture conditions. Sonicated extracts are analyzed for protein production using Western blot as previously described (Hovde et al. (1988) Proc. Nat. Acad. Sci. U.S.A. 85:2568–72).

The probiotic E. coli expressing Stx1A can be orally administered to (1) BLV-infected cows at the asymptomatic stage of infection, (2) BLV-infected cows at the PL stage of infection, (3) BLV-infected cows at the malignant lymphosarcoma stage of infection, and (4) uninfected cows.

In order to determine the effective dose of Stx1A, the titers of anti-BLV antibodies in treated cows are measured at regular intervals after the start of the treatment protocol. In addition, PBMC are isolated from treated cows and proliferation assays and BLV expression assays are performed as described in EXAMPLE 1.

Example 3

Suppression of Bovine Leukemia Virus-Related Cell Proliferation by Administering to Cows a Transgenic Plants Expressing Stx1A In this example, the suppression of BLV-related cell proliferation by administering a representative transgenic plant expressing Stx1A is described.

Materials and Methods. The techniques of amplification of genetic sequences with the polymerase chain reaction, cutting and splicing DNA into plasmids, transformation of bacteria with plasmids, and assays for antibody binding are all well known biotechnology methods and detailed descriptions of these methods can be found in a number of texts, for example Sambrook et al. (1989) Molecular Cloning-A Laboratory Manual, Cold Spring Harbor Laboratory, Cold Spring Harbor, N.Y.

The coding sequence for Stx1A is inserted into the 30B expression vector (Shivprasad et al. (1999) Virology 255: 312–23). This tobacco mosaic virus-based expression vector contains a heterologous coat protein subgenomic mRNA promoter and a heterologous 3' nontranslated region. In previous experiments, expression regulated by this vector resulted in accumulation of up to 10% of soluble protein in leaves (Shivprasad et al. (1999) Virology 255:312–23). The techniques of amplification of genetic sequences with the polymerase chain reaction (PCR), cutting and splicing DNA into plasmids, transformation of bacteria with plasmids, and assays for antibody binding are all well known biotechnology methods and detailed descriptions of these methods can be found in a number of texts including Sambrook et al. (1989) Molecular Cloning-A Laboratory Manual, Cold Spring Harbor Laboratory, Cold Spring Harbor, N.Y.

Tobacco plants and Chenopodium quinoa plants are infected with the Stx1A expression construct as previously described (Lewandowski & Dawson (1988) Virology 251:

427–37). To prepare DNA for the transcription reaction, 25 µg of the plasmid are linearized with the appropriate restriction enzyme and purified by phenol/chloroform extraction and ethanol precipitation to remove all RNAases. The DNA is then resuspended in water to a concentration of 1.25 to 2.5 µg in a volume of 12 µl. The transcription reaction cocktail contains 2.5 µl of 10×Ty RNA polymerase buffer (New England Biolabs), 2.5 µl 100 mM DTT (Gibb BRL), 0.5 µl Rnasin (Promega), 1.25 µl 10×NTPs (ATP, CTP, UTP: 20 mM, GTP: 2 mM; Amersham-Pharmacia), 4.0 µl 25 mM $MgCl_2$ (Gibb BRL), 1.25 µl 5 mM cap analogue (Diguanosine Triphosphate; Amersham-Pharmacia), and 1.25 to 2.5 µg of linearized plasmid DNA. The reaction is mixed and incubated at 37° C. for 2 minutes, after which 1 µl of T7 RNA polymerase (New England Biolabs) is added. The reaction is further incubated at 37° C. for 15 minutes, then 2 µl of 12.5 mM GTP is added. This is followed by incubation at 37° C. for an additional 75 minutes. For plant inoculation, plants are kept in the dark overnight prior to dusting. 25 µl of DEPC-treated water and 50 µl of FES buffer are gently mixed. Prior to inoculation, the leaves are dusted with carborundum. 10–15 µl of the transcription reaction is rubbed on to each leaf of the plant.

The expression of Stx1A in transgenic plants is demonstrated by Western analysis or Ouchterlonay. Fresh plant tissue is weighed and frozen at −80° C. or liquid nitrogen. The tissue is then ground with a mortar and pestle until it is powderized. To this powder, PBST (50 mM phosphate/140 mM NaCl/0.05% Tween 20, pH 7.2) is added to a final concentration of 0.5M PBST per gram and thoroughly ground. About 1.2 ml of the mixture is then transferred to a microfuge tube and centrifuged at 14,000 rpm for 10 minutes at 4° C. For Ouchterlonay, 20 µl is added per well. For Western analysis, 200 µl is mixed with 50 µl SDS loading buffer and 20–25 µl is added per well. Subsequent Western analyses are performed according to standard protocols.

The transgenic plants expressing Stx1A can be orally administered to (1) BLV-infected cows at the asymptomatic stage of infection, (2) BLV-infected cows at the PL stage of infection, (3) BLV-infected cows at the malignant lymphosarcoma stage of infection, and (4) uninfected cows.

In order to determine the effective dose of transgenic plants expressing Stx1A, the titers of anti-BLV antibodies in treated cows are measured at regular intervals after the start of the treatment protocol. In addition, PBMC are isolated from treated cows and proliferation assays and BLV expression assays are performed as described in EXAMPLE 1.

Example 4

Suppression of Bovine Leukemia Virus-Related SLP by Administering Stx2 Holotoxin and Analyses of Stx1A Mutants In this example, the suppression of BLV-related spontaneous lymphocyte proliferation by administering purified Stx2 holotoxin is described and the enzymatic and antiviral activities of three Stx1A mutants, deficient enzymatic activity or aspects of receptor-mediated cytotoxicity, are compared.

Shiga-toxins have a single enzymatically active ~32 kDa A subunit non-covalently associated with a pentamer of ~7.7 kDa B subunits. The A subunit is an N-glycosidase that cleaves a specific adenine residue on 28S rRNA in 60S ribosomal subunits (Donahue-Rolfe et al. (1991) *Rev. Infect. Dis.* 13(Suppl. 4):S293–7; Hartley et al. (1991) *FEBS Lett.* 290:65–8), and the pentamer of B subunits mediates binding of holotoxin to toxin receptors. Stx1 and Stx2 bind to globotriosylceramide (Gb3) (Jacewicz et al. (1986) *J. Exp. Med.* 163:1391–404; Junqua et al. (1987) *Eur. J. Immunol.* 17:459–64) expressed by Vero cells and also by other types of sensitive cells, including human renal endothelial cells (Obrig et al. (1993) *J. Biol. Chem.* 268:15484–8). Following internalization, toxin enters the cytosol via retrograde transport from the trans-Golgi network (Sandvig et al. (1994) *J. Cell. Biol.* 126:53–64). The A chain is proteolytically cleaved into a 27.5 kDa $A_1$ fragment (enzymatically active) and a small $A_2$ fragment that, in an intact A chain, obstructs access to the catalytic center and mediates A:B association (Austin et al. (1994) *Infect. Immun.* 62:1768–75; Fraser et al. (1994) *Nat. Struct. Biol.* 1:59–64). Thus, receptor-mediated cytotoxicity of Shiga-toxins requires an enzymatically active A chain capable of association with B subunits and able to complete retrograde transport into the cytosol. Consequently, Stx1 A chain (Stx1A) mutations that abrogate receptor-mediated Stx1 cytotoxicity include mutations in the catalytic center, mutations that render the A chain unable to associate with B subunits, or mutations within a hydrophobic region of Stx1A required for cell trafficking.

Three Stx1A mutants, each one deficient in a different aspect of receptor-mediated cytotoxicity, were analyzed for antiviral activity. The enzymatic mutant E167D has several hundred-fold lower enzymatic activity than wild-type Stx1A due to a substitution within the catalytic center of a glutamic acid 167 to an aspartic acid (Hovde et al. (1988) *Proc. Nat. Acad. Sci. U.S.A.* 85:2568–72). The cell-trafficking mutant, A231D-G234E, is enzymatically active but crippled in retrograde transport due to substitutions outside of the catalytic center of an alanine 231 to an aspartic acid and a glycine 234 to a glutamic acid (Suhan & Hovde (1998) *Infect. Immun.* 66:5252–9). The association mutant Stx1$A_1$ is enzymatically active but unable to associate with B subunits due to a deletion of 39 amino acids at the carboxy terminus (Austin et al. (1994) *Infect. Immun.* 62:1768–75). The findings described in this Example demonstrate that Stx2 holotoxin suppresses BLV-related sponteaneous lymphocyte proliferation. In addition, it is shown that the enzymatic mutant E167D was minimally active in antiviral assays, and did not inhibit synthesis of viral proteins, and that the cell-trafficking mutant A231D-G234E and the association mutant Stx1$A_1$ had undiminished viral activity.

Materials and Methods. Holstein cows naturally infected with BLV were from the dairy herd of the University of Idaho (Moscow, Id.). These BLV-positive cattle were seropositive for antibody to the BLV protein gp51 by agar gel immunodiffusion and were in an advanced (persistently lymphocytotic) subclinical stage of disease (Bendixen (1965) *Adv. Vet. Sci.* 10:129–204). BLV-negative cattle were from the BLV-free herd at Washington State University Knotts Dairy Center (Pullman, Wash.), were seronegative for BLV, and maintained normal white blood cell counts.

Wild-type and mutants of Stx1A were purified using previously described methods (Hovde et al. (1988) *Proc. Nat. Acad. Sci. USA.* 85:2568–72; Suhan & Hovde (1998) *Infect. Immun.* 66:5252–9; Zollman et al. (1994) *Prot. Expr. Purif.* 5:291–295). Briefly, periplasmic proteins were extracted from recombinant *E. coli* by treatment with polymyxin B sulphate (50 µg/ml), concentrated by 80% ammonium sulphate precipitation, dialyzed, and adsorbed to a Matrex Gel Green A agarose column (Amicon, Mass., USA) equilibrated with 10 mM phosphate-buffered saline (PBS). The toxins were eluted at ~0.3 M NaCl using a gradient of 0.15 to 1.0 M NaCl. Toxins were dialyzed against 10 mM PBS, and their concentrations were measured using a Bio- Rad microassay with bovine serum albumin as a standard. Wild-type Stx1A was purified from *E. coli* SY327(pSC25) (Hovde et al. (1988) *Proc. Nat. Acad. Sci. U.S.A.* 85:2568–72), the enzymatic mutant E167D from *E. coli* SY327(pSC25.1) (Hovde et al. (1988) *Proc. Nat. Acad. Sci. U.S.A.* 85:2568–72), the cell-trafficking mutant A231D-G234E from *E. coli* SY327(pUC$^A$H25) (Suhan & Hovde (1998) *Infect. Immun.* 66:5252–9), and the A:B association mutant Stx1A$_1$ was purified from *E. coli* DH5α(pRD500) (Austin et al. (1994) *Infect. Imm.* 62:1768–75). Wild-type Stx2 holotoxin was a gift from Dr. A. D. O'Brien (Uniformed Services University of the Health Sciences, Bethesda, Md.) (Kokai-Kun et al. (2000) *J. Biol. Chem.* 275:3713–21).

Enzymatic activity of the toxins was measured in a protein synthesis inhibition assay using a Luciferase Assay System (Promega Corporation, Madison, Wis.) according to the manufacturer's instructions. Briefly, various amounts of purified toxins in PBS were pre-incubated with rabbit reticulocyte lysate at 30° C. for 20 min. Following pre-incubation, the lysates were combined with leucine-free and methionine-free amino acid mix, RNasin ribonuclease inhibitor, luciferase RNA, and nuclease-free water. Protein synthesis was allowed to proceed for 90 min, an aliquot of the reaction mixture was combined with Luciferase Assay Reagent, and the resulting chemiluminescence was measured over a 10 second period with a 2 second delay, using a luminometer (Lumat LB 9507; Berthold Technologies U.S.A., Oak Ridge, Tenn.).

Blood was collected from cows in acid citrate dextrose (1 part to 4 parts of blood). Peripheral blood mononuclear cells (PBMC) were purified as described previously (Ferens & Hovde (2000) *Infect. Imm.* 64:4462–9). Briefly, buffy coat cells were separated by centrifugation on Accu-Paque™ Lymphocytes of density 1.086 g/ml (Accurate Chemical and Scientific Corp., Westbury, N.Y.). PBMC were washed thrice in Hank's Balanced Salt Solution (HBBS) (Sigma, St. Lois, Mo.) supplemented with 2% heat-inactivated fetal bovine serum (FBS) (HyClone, Logan, Utah) at 4° C. The cells were cultured in 96-well culture plates (Corning, New York, N.Y.) seeded with $0.5 \times 10^6$ cells/well at a final density of $2.5 \times 10^6$ cells/ml in RPMI 1640 (Invitrogen, Carlsbad, Calif.) supplemented with 20% FBS, 2 mM L-glutamine, 100 U/ml of penicillin, and 100 µg/ml of streptomycin. DNA synthesis was assayed by incorporation of $^3$H-thymidine (Perkin Elmer Life Sciences, Boston, Mass.) added in the amount of 1.0 mCi/well 48 h after cell culture commencement and 16 to 18 h prior to cell harvest. Cells were harvested on a semi-automated 96-well plate harvester (Skatron Inc., Sterling, Va.), the amount of incorporated $^3$H-thymidine was determined by liquid scintillation spectroscopy (Packard Instrument Co., Downers Grove, Ill.), and expressed as counts per minute (CPM). The proliferation assays were done in quadruplicate and percentage inhibition of proliferation was expressed as (CPM of cultures with toxin/CPM of cultures without toxin)×100.

Polyclonal antibody to Stx1A was generated by standard technique in New Zealand White rabbits. Murine monoclonal antibodies were obtained from the Washington State University Monoclonal Antibody Center (Pullman, Wash.). Antibodies specific for bovine B-cell markers recognized B-B1 (BAS9A, IgM), B-B2 (BAQ44A, IgM), or CD21-like (GB25A, IgG$_1$) antigens, and antibody specific for T-cell marker recognized bovine CD3 (MM1A, IgG$_1$). Monoclonal antibodies against BLV were specific for a capsid protein p24 (MW3, IgG$_1$), or for an envelope glycoprotein gp51 (MW1, IgG$_1$). Control antibody was mouse IgG1 specific for *E. coli* glycoproteins (coliS 69A).

For the BLV expression assay, two ml aliquots of PBMC ($0.5 \times 10^6$ cells/ml) were placed in culture dishes with or without 0.5 µg/ml toxin. The harvested cultures were separated by centrifugation into cells and cell-free supernatants to analyze cell-associated virus and cell-free virus, respectively. The cells were processed by repeated freeze-thaw cycles in 0.5 ml of 0.1 M Tris buffer (pH 7.5) with 0.1 M EDTA and 0.1 M phenylmethylsulfonyl fluoride and complete lysis was determined microscopically. The cell lysates and the cell culture supernatants were transferred to nitrocellulose using a 96-well blotter (Schleicher and Schuell, Keene, N. H.). The membranes were probed with antibodies against BLV proteins p24 and gp51, followed by anti-mouse antibody conjugated to alkaline phosphatase. Immunoblots were developed using 5-bromo-4-chloro-3-indolylphosphate and nitroblue tetrazolium as substrate, according to manufacturer's instructions, and scanned with a Hewlett-Packard densitometer. The results were quantitated with the Molecular Analyzer analytical program. Cultures of PBMC from BLV-free cattle served as negative controls.

Stx2 had antiviral, activity similar to Stx1. To determine whether antiviral activity is common to the Shiga-toxins prevalent in cattle, Stx2 holotoxin (~70 kDa) was tested for its ability to suppress BLV-dependent cell proliferation and compared to Stx1A (~32 kDa). To ensure that the toxins were enzymatically active, they were tested in a protein synthesis inhibition assay. On a molar basis, Stx2 was 2.5-fold less enzymatically active than Stx1A when compared for 50% protein synthesis inhibition (regression analysis, not shown) FIG. 5A). Antiviral activity was measured as inhibition of SLP (FIG. 5B). Stx2 had slightly more antiviral activity than Stx1A, since 4-fold less Stx2 than Stx1A, on a molar basis, inhibited cell proliferation by 50%. These results indicate that Stx1 and Stx2 had similar enzymatic and antiviral properties. Although the antiviral effects of Stx in vitro do not require the Gb3-binding B subunit (Ferens & Hovde (2000) *Infect. Imm.* 64:4462–9), both Stx1 and Stx2 holotoxins were more potent on a molar basis than the A chain alone. This could be due to numerous factors that were not measured such as differential proteolysis, loss of enzymatic activity, and/or differences in cell internalization.

The finding that both Stx1 and Stx2 had antiviral activity in vitro buttresses a conjecture of antiviral activity in animals carrying STEC. This finding is consistent with research showing the cytotoxic activity of plant RIPs against virally infected animal cells (Fernandez-Puentes (1984) *Mol. Biol. Rep.* 10:65–8; Fernadez-Puentes & Carrasco (1980) *Cell* 20:769–75) and the work showing that RIPs have antiviral activity for the plants that synthesize them (Stirpe et al. (1992) *Biotechnology* (NY) 10:405–12). Cattle are transiently colonized at various times by STEC expressing Stx1, Stx2, and/or Stx2 variants in some combination. Toxins can be detected in fecal samples from cattle, indicating that STEC express toxin in vivo (Hyatt et al. (2001) *J. Vet. Diagn. Invest.* 13:71–3), and individual cattle are likely exposed to Shiga-toxins in their gastrointestinal tract. Shiga-toxins translocate through the human intestinal epithelium (Acheson et al. (1996) *Infect. Immun.* 64:3294–3300), and therefore may have similar ability in the bovine gastrointestinal mucosa. The notable lack of Stx detrimental effects in cattle is likely due to the absence of Gb3 in the bovine vasculature (Pruimboom-Brees et al. (2000) *Proc. Natl. Acad. Sci. U.S.A.* 97:10325–9); however, the recent finding of Gb3 on bovine crypt epithelial cells in the small and large intestine indicates that Shiga-toxin binding plays a role in STEC intestinal colonization (Hoey et al. (2002) *J. Med. Microbiol.* 51:143–9) and may facilitate transport of toxin systemically. Reports of cattle colostral antibodies to Stx1 and Stx2 (Pirro et al. (1995) *Vet. Microbiol.* 43(2–3):131–41) indicate that the toxins leave the bovine intestinal lumen and are processed by the cells of the mucosa-associated lymphatic system. Also, reports of neutralizing antibodies to Stx1 in serum indicate systemic exposure to this toxin (Pirro et al. (1995) *Vet. Microbiol.* 43(2–3):131–41; Johnson et al. (1996) *Infect. Immun.* 64:1879–83); possibly, these antibodies may remove toxin in sensitized animals. However, anti-Stx2 neutralizing antibodies are not detected in serum (Pirro et al. (1995) *Vet. Microbiol.* 43(2–3):131–41; Johnson et al. (1996) *Infect. Immun.* 64:1879–83) so that this toxin does not enter the circulation or, more likely, does not elicit a systemic immune response. Thus, lymphocytes may interact with Stx in the intestinal mucosa and/or in the systemic circulation.

Figure 5:
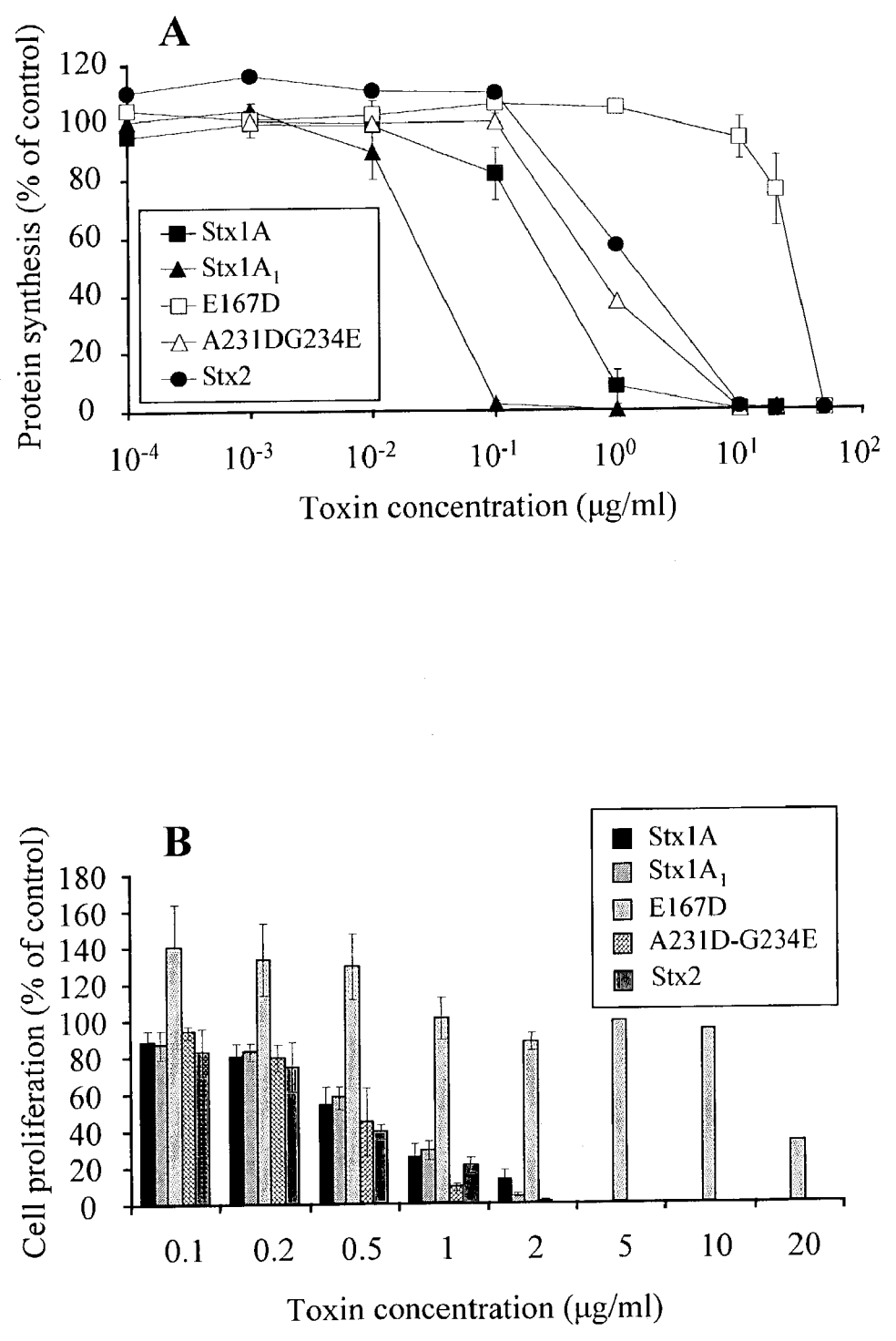

Enzymatically active Stx1A mutants retained antiviral activity in spite of a loss of receptor-mediated toxicity. The observation that the antiviral activity of Stx1 did not require the Stx1 B subunit (Ferens & Hovde (2000) *Infect. Imm.* 64:4462–9) prompted an investigation into whether mutations of Stx1A, that abrogate receptor-mediated cytotoxicity towards Vero cells and other Gb3-expressing cells (Suhan & Hovde (1998) *Infect. Immun.* 66:5252–9), would also affect the antiviral activity of Stx1A. Thus, the ability of three well-defined Stx1A mutants to inhibit protein synthesis and suppress SLP were analyzed (FIG. 5). The enzymatic mutant E167D had 300-fold less activity than Stx1A when compared for 50% protein synthesis inhibition, and its ability to inhibit protein synthesis was significantly different from that of the other toxins at concentrations ranging from 1.0 to 20 μg/ml (p<0.01, ANOVA) (FIG. 5A). The enzymatic activity of the A:B association mutant Stx1A$_1$ land the cell-trafficking mutant A231D-G234E were both similar to that of wild-type Stx1A (FIG. 5A). The former required 2.3-fold lower molar concentration and the latter required the same molar concentration as wild-type Stx1A for 50% inhibition protein synthesis.

The antiviral activity of the toxins was tested in a SLP suppression assay and expressed as the ability to suppress BLV-dependent cell proliferation (FIG. 5B). The antiviral activity of the mutant toxins was associated with enzymatic activity, but not with other functional characteristics. The mutants that retained undiminished enzymatic activity (Stx1A$_1$ and A232D-G234E) suppressed SLP as effectively as wild type Stx1A. Thus, neither of the mutations located outside of the catalytic center decreased antiviral activity of the toxins, in spite of abrogating the ability of mutant toxin to associate with B subunits (Stx1A$_1$) or to undergo retrograde transport within intoxicated cells (A232D-G234E). The less active enzymatic mutant E167D had reduced antiviral activity, and required a 40-fold higher concentration than other toxins to inhibit cell proliferation by 50%. Interestingly, this molecule not only did not inhibit cell proliferation at concentrations <10 μg/ml, but at concentrations ranging from 0.1 to 0.5 μg/ml it consistently increased proliferation by 35–40% compared to the control.

The finding that the enzymatic activity of Stx was necessary for antiviral activity is similar to data showing that plant RIPs must maintain enzymatic activity to exert antiviral impact (Stirpe et al. (1992) *Biotechnology* (NY) 10:405–12; Turner et al. (1997) *Proc. Natl. Acad. Sci. U.S.A.* 94:3866–71; Wang & Turner (2000) *Adv. Virus Res.* 55:324–55). The substrate for this enzymatic activity was not identified, but it may be the host cell ribosome or viral nucleic acid(s). Recent studies showed that mutant pokeweed antiviral protein devoid of anti-ribosomal activity but capable of depurinatation of capped mRNA transcripts retain antiviral activity (Hudak et al. (2000) *RNA* 6:369–80). The requirement for enzymatic activity was demonstrated using the well-characterized E167D mutant that contains a conservative substitution (aspartic acid for a glutamic acid at position 167) to disable the catalytic center without significantly altering molecular integrity (Hovde et al. (1988) *Proc. Natl. Acad. Sci. U.S.A.* 85:2568–72).

The A:B association mutant Stx1A$_1$ has enhanced enzymatic activity because it lacks 38 carboxy terminal amino acids (Austin et al. (1994) *Infect. Immun.* 62:1768–75) that block the catalytic center in full-length A chain (Fraser et al. (1994) *Nat. Struct. Biol.* 1:59–64). In spite of the fact that Stx1A$_1$ was enzymatically more active than wild-type Stx1A or the cell-trafficking mutant A231D-G234E, it did not have more antiviral activity than these toxins. Although toxin stability was not measured, the A:B association mutant Stx1A$_1$ may have been more susceptible to degradation in culture medium and/or inside intoxicated cells than the other toxins. Also, the assay method may not have been sensitive enough to detect differences in antiviral activity that might result from several-fold difference in enzymatic activity.

The molecular motifs required for receptor-mediated cytotoxicity of Shiga-toxins were not necessary for antiviral effect. Both the Stx1A$_1$ mutant, unable to associate with B subunits, and the A231D-G234E mutant, crippled in cell-trafficking ability, had antiviral activity similar to that of a wild-type Stx1A. These results are consistent with the antiviral activity of the ricin A chain and of RIP hemitoxins (Lee-Huang et al. (1991) *Proc. Natl. Acad. Sci. U.S.A.* 88:6570–4; Olson et al. (1991) *AIDS Res. Hum. Retroviruses* 7:1025–30). Furthermore, antiviral activity of Stx1A$_1$ and of A231D-G234E mutants, devoid of receptor-mediated cytotoxicity towards Vero cells, pointed to the direct absorption, of toxins by virus-expressing cells as a possible mechanism of target cell intoxication.

Figure 6:
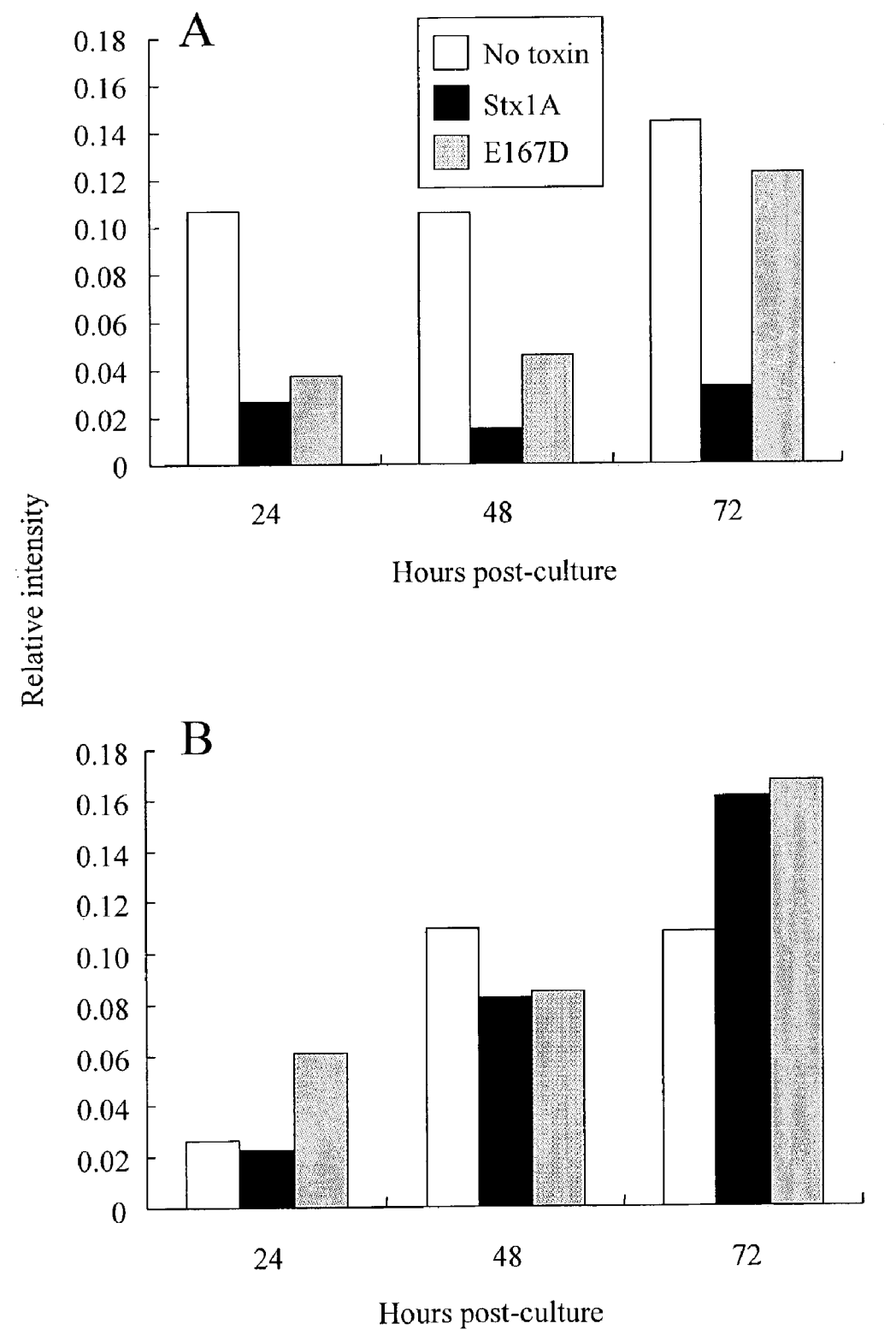

Stx1A enzymatic activity was required for suppression of BLV protein expression. The impact of Stx1A on viral protein expression was assessed by measuring the amounts of BLV proteins p24 and gp51 in cell culture. PBMC from BLV-positive cattle were cultured with wild-type Stx1A, enzymatic mutant E167D, or without toxin and BLV proteins were measured. Harvested cultures were separated into cells and cell-free supernatants to measure cell-associated and cell-free viral proteins, respectively (FIG. 6). Cell-associated BLV proteins were not detectable in ex vivo PBMC by immunoblotting, but could be detected 12 h post-culture (relative intensity of 0.04). Twenty-four h post-culture and later, cell-associated BLV proteins were prominent in control cultures not treated with toxin, apparent in cultures treated with the enzymatic mutant E167D, but barely detectable in cultures treated with Stx1A (FIG. 6A).

In contrast to BLV protein expression associated with cells, the cell-free supernatants from cultures incubated with toxins contained either similar amounts (48 h) or greater amounts (72 h) of BLV proteins, compared to control cultures (FIG. 6B). The finding that Stx1A-treated cultures harvested at 48 h and 72 h contained small amounts of BLV proteins associated with cells but high amounts of BLV proteins in the culture supernatants suggests that the interaction of Stx1A with target cells interrupted virion assembly, induced cell death and/or loss of membrane integrity to a much greater extent than E167D. Such a possibility would be consistent with results from flow cytometric analysis that suggested the percentage of BLV-expressing cells was reduced in cultures treated with Stx1A, but not in cultures treated with the enzymatic mutant E167D or without toxin.

Example 5

Flow Cytometric Analyses of BLV-Expressing Cells from Cultures Treated with Stx

In this example, flow cytometry analyses of BLV-expressing cells from cultures treated with Stx are described.

Natural BLV infections in cattle was used as a model to study the impact of toxin on viral activity. Removal of PBMC from autologous serum, containing specific antibody against BLV, precipitates a chain of events in which provirus becomes derepressed and viral protein synthesis and virus release occurs. The number of cells expressing virus ex vivo is <2% and upon culture this proportion may increase. Viral derepression is accompanied by SLP, a rapid proliferation of a small number of B cells (and some T cells) that are not expressing virus. The highest number of replicating cells can be measured 72 h post-culture. SLP can be blocked by treating cultures with toxin within 12 h, but has little effect if added later (Ferens & Hovde (2000) Infect. Immun. 68:4462–9). Thus, toxin interferes with the initiation of SLP, but has little effect on the subsequent proliferation of cells that do not express virus. One hypothesis is that only the rare BLV-expressing cells are sensitive to toxin because viral synthesis increases membrane permeability of these cells allowing toxin entry, with ensuing inhibition of viral protein synthesis and abrogation of SLP. The findings described in this example suggest that Stx may be a factor in limiting BLV infection in cattle to a chronic well-tolerated disease rather than an acute deadly disease.

Material and Methods. Purified Stx1A was iodinated using Iodo-Beads (Pierce Endogen, Rockford, Ill). One bead was incubated for 7 min at room temperature with 0.5 mCi of carrier-free $Na^{125}I$ (Amersham Pharmacia Biotech, Piscataway, N.J.) and 10 µg of Stx1A in 100 µl of 50 mM sodium phosphate, pH 7.4. Labeled Stx1A was separated from free iodine using a Bio-Gel P-10 column (Bio-Rad Laboratories, Hercules, Calif.) equilibrated with PBS. The specific radioactivity of the labeled toxin ranged from 3 to 30 µCi/µg. The iodinated toxin was tested for its enzymatic activity in a protein synthesis inhibition assay (see EXAMPLE 4) with unlabeled toxin as a control. PBMC, granulocytes, and erythrocytes from BLV-positive and BLV-negative cattle at concentrations of $2 \times 10^7$ cells/ml were incubated with 0.5 µg/ml of the iodinated toxin for 60 min, at 4° C. or at 37° C. to prevent or to allow active internalization, respectively. The harvested cells were collected onto GF/B membranes (Whatman International Ltd, Maidstone, England) pre-soaked in 0.3% polyethyleneimine. Radioactivity of filter membranes (containing bound toxin) and of filtrates (containing free toxin) was measured in a COBRA II gamma counter (Packard Instruments, IL, USA).

BLV virions were prepared from a BLV-infected bat lung cell line, $BLV-bat_2$, as previously described (Stone et al. (2000) Clin. Immunol. 96:280–8). Virions were tested directly (dot blots) or the antigen was concentrated and fractioned electrophoretically on polyacrylamide gel and transferred to nitrocellulose. Blots were probed with Stx1A followed by rabbit polyclonal anti-Stx1A antibody and anti-rabbit antibody conjugated to alkaline phosphatase. Immunoblots were developed and scanned as described in EXAMPLE 4, above.

Staining and formaldehyde fixation of cells for flow cytometric analysis was performed in 96-well plates using a standard protocol (Stone et al. (2000) J. Gen. Virol. 81(4): 971–81). Second-step reagents were goat anti-mouse antibodies conjugated to fluorescein isothiocyanate (FITC), R-phycoerythrin, and Tricolor (Caltag, Burlingame, Calif.). Data were acquired on a FACSCalibur flow cytometer (Becton Dickinson Immunocytometry Systems, San Jose, Calif.) with a 488 nm argon laser. Viable and non-viable cells were gated on the basis of forward and side scatter. Results were analyzed using Becton-Dickinson analytical software (CellQuest and Attractors).

Permeability of cells to macromolecules was assayed with fluorescein-conjugated lysine-fixable dextrans of 3 kDa, 40 kDa, and 70 kDa molecular weight (mw) (Molecular Probes, Eugene, Oreg.). One million cells suspended in 100 µl of RPMI 1640 with 10% FBS (RPMI/10% FBS) was added to a mixture containing 50 µl of 15 µg/ml primary antibody to cell surface molecules in HBSS, 20 µl of 10 mg/ml dextran solution in HBBS, and 30 µl of RPMI/10% FBS. Cells were incubated for 60 min on ice to allow passive uptake of dextrans, washed, incubated for 20 min on ice in 100 µl of RPMI/10% FBS with secondary antibodies, washed, and fixed with 2% formaldehyde in PBS. Control samples were incubated without dextrans or without second-step antibodies. All washes were done with PBS supplemented with 2% gamma-globulin-free horse serum. Cells exhibiting green fluorescence of 1.1 log or greater were considered positive for dextran. Typically, 50,000 cells were collected per sample.

The results are presented as arithmetic means±standard errors (SE) of three or more replicates. Results of the protein synthesis inhibition assays were analyzed using a linear regression. Results of the permeability assays were analyzed by ANOVA, after cosign transformation of percentages expressed as values ranging from 0 to 1, using MINITAB statistical analysis software (Minitab, Inc.).

Stx1A did not bind to bovine blood cells or to viral particles. To test whether Stx1A binds to corpuscular blood components, whole blood from BLV-positive and BLV-negative cattle was fractionated by density-centrifugation into PBMC, granulocytes, and erythrocytes and the fractions were incubated with a $^{125}I$-labeled Stx1A. The enzymatic activity of radiolabeled toxin was similar to that of the unlabeled toxin in the protein synthesis inhibition assay, indicating that iodination did not disrupt the molecular structure of Stx1A. Leucocytes and erythrocytes from BLV-negative and BLV-positive cattle did not bind appreciable amounts of the radiolabeled toxin. Notwithstanding that Stx1A entry into target cells would be necessary to suppress SLP or viral protein synthesis, it is likely that direct assessment of toxin entry into cells using radiolabeled toxin was beyond the limits of sensitivity of the assay, due to the scarcity of BLV-expressing cells (<2% in ex vivo PBMC). In addition, toxin binding to virions was assessed in dot blots of BLV virus and immunoblots of concentrated viral antigens probed with Stx1A. No binding was detected. Thus, the results of all toxin binding measurements support the contention that Stx1A interacts with selected and rare cellular targets in PBMC cultures.

Flow cytometric analysis suggests that the numbers of BLV-expressing cells (cell positive for the BLV protein gp5 on their surface) were reduced in cultures treated with Stx. Although the identity of the cells targeted by Shiga-toxins in the course of SLP suppression was not unequivocally established, previous results indicate that the antiviral action of Shiga-toxins is not indiscriminate and targets select and infrequent cells (Ferens & Hovde (2000) Infect. Immun. 68:4462–9). This is supported by the present findings that Stx1A did not bind to bovine erythrocytes, bovine leukocytes, or to free virus. Although flow cytometric analysis suggested the BLV-expressing cells in PBMC cultures are eliminated by Stx1A, it was not possible to detect absorption of radiolabelled Stx1A by the BLV-expressing cells or any other cells in PBMC culture. This might be ascribed to the following constraints. First, the proportion of BLV-expressing cells (the presumptive targets) in culture was very low (<2% of BLV protein-positive cells in uncultured ex vivo PBMC from BLV-positive cattle), limiting the ability to analyze them directly. Second, the toxin exerts a lethal cytotoxic effect at extremely low intra-cellular concentrations and may have killed the target cells before they accumulated a detectable amount of the toxin. Thirdly, the loss of BLV-expressing cells during incubations and washings was proportionally greater than the loss of other cells.

BLV-expressing cells were highly permeable to macromolecules. Although the possibility of receptor mediated binding of the A subunit to bovine PBMC is not excluded, the finding that suppression of BLV-dependent SLP occurred in cultures treated with either the isolated Stx1 A chain, devoid of receptor-binding B subunits, or with the cell-trafficking mutant A231D-G234E, crippled in retrograde transport, strongly indicated that the toxin enters the cytosol of target cells directly. Because virally infected cells often exhibit increased permeability to macromolecules due to virus-induced alterations in cell membrane (reviewed in Carrasco (1995) Adv. Virus Res. 45:61–112), it was hypothesized that entry of Stx1A into the relatively rare cellular targets in PBMC cultures involved increased permeability of the cells expressing BLV. Accordingly, the permeability of PBMC from BLV-positive cattle was assessed using flow cytometry. The cells were stained with Tricolor labeled monoclonal antibody MW1, specific for BLV surface unit glycoprotein 51,000 MW (gp51), and incubated with fluorescein-conjugated 40 kDa dextran to compare permeability of PBMC negative and positive for gp51. Cells expressing gp51 on their surface are engaged in virion assembly, cells not expressing gp51 are not expressing virus. In three separate experiments, PBMC from 3 BLV-positive cattle were gated on the basis of gp51 expression and their permeability was assessed by measuring green fluorescence. Cells exhibiting green fluorescence above 1.1 log were considered dextran-positive, and were divided arbitrarily into cells exhibiting low fluorescence (1.1 to 2.05 log) and high fluorescence (2.05 log to 3.7 log). Cell not expressing virus (gp51-negative) were rarely permeable to dextran as 2.2%, 10.1%, and 13.7% of these cells exhibited low green fluorescence and 0.8%, 2.2%, and 1.1% of these cells exhibited high green fluorescence (values from three animals, respectively). In contrast, cells expressing virus (gp51-positive) consistently internalized dextran as 9.8%, 20.0%, and 33.8% of these cells exhibited low green fluorescence and 14.1%, 16.6%, and 15.2% exhibited high green fluorescence (values from three animals, respectively). These data are representative of three experiments per animal.

Because of the high degree of BLV tropism for B cells, gp51-positive PBMC are comprised primarily of B lymphocytes, whereas gp51-negative PBMC contain B lymphocytes and other categories of mononuclear blood cells. Thus, comparing permeability of total PBMC could produce biased results, since BLV rarely infects cells other than B lymphocytes (Esteban et al. (1985) Cancer Res. 45:3225–30; Schwartz et al. (1994) J. Virol. 68:4589–96). Accordingly, the permeability of the total B-cell population was compared with the permeability of gp51-positive cells and T cells, using dextrans of 3 kDa, 40 kDa, and 70 kDa mw (Table 2; FIG. 7). The fact that similar proportions of gp51-positive cells were permeable to 40 kDa and 70 kDa dextrans (Table 2; FIGS. 7B and 7C) indicates that a direct absorption of toxin into the cytosol via the cell membrane is an entry route potentially accessible to the isolated A chain of Stx1 (~32 kDa), and also to Stx1 holotoxin (~70 kDa).

TABLE 2

Permeability of B cells, gp51-positive cells and T cells to Dextrans

| Cell Type | MW of Dextran (kD) | No Fluorescence (%) | Low Fluorescence (%) | High Fluorescence (%) |
|---|---|---|---|---|
| T cells | 3 | 86.6 | 11.6 | 1.8 |
|  | 40 | 92.9 | 6.1 | 1.0 |
|  | 70 | 95.4 | 4.4 | 0.2 |
| B cells | 3 | 59.6 | 35.6 | 4.8 |
|  | 40 | 87.0 | 10.0 | 3.0 |
|  | 70 | 90.1 | 9.5 | 0.4 |
| gp51+cells | 3 | 44.3 | 49.4 | 6.3 |
|  | 40 | 80.5 | 16.4 | 3.1 |
|  | 70 | 75.9 | 22.2 | 1.9 |

The permeability of total B cells from BLV-positive cattle to dextrans was lower than the permeability of gp51-positive cells, but higher than the permeability of T cells, which rarely exhibited green fluorescence above background, even after incubation with low mw dextran (Table 2; FIG. 7A). Since the B cells from BLV-positive cattle with persistent lymphocytosis exhibit abnormal characteristics (Stone et al. (1995) Vet. Immunol Immunopathol. 48:65–76; Stone et al. (1994) Leukemia 8:1057–61) and cannot be considered normal, it was important to compare the permeability of B cells from BLV-positive cattle with the permeability of B cells from BLV-negative cattle (FIG. 8). The latter cells consistently showed miniscule permeability to dextrans, whereas the permeability of total B cells from BLV-positive cattle was consistently greater, indicating that not only BLV-expressing cells, but also some other B cells from these animals may have been permeable and sensitive to toxin.

Thus, increased permeability of BLV-expressing cells to toxins may be involved in SLP suppression, and may explain the sensitivity of these cells to Stx. Although toxin entry into cells was not measured, it was shown that BLV-expressing cells were permeable to 70 kDa molecules, and that the permeability of B lymphocytes from cattle with BLV-induced persistent lymphocytosis greatly exceeded the permeability of B cells from BLV-negative cattle. From these results it is hypothesized that the cells that express BLV constitute the primary targets of Shiga-toxins. In addition, some B cells from BLV-positive cattle (not expressing BLV but permeable to macromolecules) may be secondary target cells, since most of these cells contain BLV provirus (Mirsky et al. (1996) *J. Virol.* 70:2178–83) and are physiologically abnormal (Stone et al. (1995) *Vet. Immunol. Immunopathol.* 48:65–76; Stone et al. (1994) *Leukemia* 8:1057–61).

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for eliminating virally-infected cells in a mammalian subject, comprising administering to a mammalian subject infected with a virus an amount of a Shiga-toxin composition consisting essentially of a Shiga-toxin A subunit or an euzymatically-active portion thereof effective to eliminate virally-infected cells, and an acceptable carrier.

2. The method of claim 1, wherein the Shiga-toxin composition comprises subunit A of Stx1.

3. The method of claim 1, wherein the Shiga-toxin composition comprises subunit A of Stx2.

4. The method of claim 1, wherein the virus is at least one of semliki forest virus, vesicular stomatitis virus, vaccinia, adenovirus, polio virus, picorna virus, togavirus, reovirus, respiratory syncitial virus, hepatitis virus, coronavirus, rotavirus, influenza virus, herpes virus, bovine leukemia virus, bovine immunodeficiency virus and human immunodeficiency virus.

5. The method of claim 1, wherein the virus is a bovine leukemia virus.

6. The method of claim 1, wherein the mammalian subject is a ruminant.

7. The method of claim 1, wherein the mammalian subject is a human subject.

8. A method for treating a virus infection in a mammal, comprising administering to a mammal infected with a virus an amount of a Shiga-toxin composition consisting essentially of a Shiga-toxin A subunit or an enzymatically-active portion thereof effective to treat the virus infection, and an acceptable carrier.

9. The method of claim 8, wherein the Shiga-toxin composition comprises subunit A of Stx1.

10. The method of claim 8, wherein the Shiga-toxin composition comprises subunit A of Stx2.

11. The method of claim 8, wherein the virus is at least one of semliki forest virus, vesicular stomatitis virus, vaccinia, adenovirus, polio virus, picorna virus, togavirus, reovirus, respiratory syncitial virus, hepatitis virus, coronavirus, rotavirus, influenza virus, herpes virus, bovine leukemia virus, bovine immunodeficiency virus and human immunodeficiency virus.

12. The method of claim 8, wherein the virus is a bovine leukemia virus.

13. The method of claim 8, wherein the mammalian subject is a ruminant.

14. The method of claim 8, wherein the mammalian subject is a human subject.

15. A method for eliminating virally-infected cells in a ruminant, comprising administering to a ruminant infected with a virus an amount of a Shiga toxin holotoxin effective to eliminate virally-infected cells.

16. The method of claim 15, wherein the wherein the Shiga toxin is Stx1.

17. The method of claim 15, wherein the Shiga toxin is Stx2.

18. The method of claim 15, wherein the virus is bovine leukemia virus.

19. A method for treating a virus infection in a ruminant, comprising administering to a ruminant infected with a virus an amount of a Shiga toxin holotoxin effective to treat the virus infection.

20. The method of claim 19, wherein the wherein the Shiga toxin is Stx1.

21. The method of claim 19, wherein the Shiga toxin is Stx2.

22. The method of claim 19, wherein the virus is bovine leukemia virus.

* * * * *

UNITED STATES PATENT AND TRADEMARK OFFICE
CERTIFICATE OF CORRECTION

PATENT NO. : 7,135,173 B2
APPLICATION NO. : 10/325664
DATED : November 14, 2006
INVENTOR(S) : C.H. Bohach et al.

It is certified that error appears in the above-identified patent and that said Letters Patent is hereby corrected as shown below:

| COLUMN | LINE | ERROR |
| --- | --- | --- |
| On Title Page Item (56) Pg. 1, col. 2 | Refs. Cited (Other Publs., Item 2) | "Colume" should read --Volume-- |
| Item (56) Pg. 2, col. 1 | Refs. Cited (Other Publs., Item 29) | "Immunotoins:" should read --Immunotoxins:-- |
| Item (56) Pg. 2, col. 1 | Refs. Cited (Other Publs., Item 33) | "Gupta, p., et al.," should read --Gupta, P., et al.,-- |
| Item (56) Pg. 2, col. 2 | Refs. Cited (Other Publs., Item 34) | "*of*= *Virology*" should read --*of Virology*-- |
| Item (56) Pg. 2, col. 2 | Refs. Cited (Other Publs., Item 41) | "*4*343:131-141," should read --43:131-141,-- |
| Item (56) Pg. 2, col. 2 | Refs. Cited (Other Publs., Item (51) | "wntiviral" should read --antiviral-- |
| 38 (Claim 16, line 1) | 23 | delete the second occurrence of "wherein the" |

UNITED STATES PATENT AND TRADEMARK OFFICE
CERTIFICATE OF CORRECTION

PATENT NO. : 7,135,173 B2
APPLICATION NO. : 10/325664
DATED : November 14, 2006
INVENTOR(S) : C.H. Bohach et al.

It is certified that error appears in the above-identified patent and that said Letters Patent is hereby corrected as shown below:

| COLUMN | LINE | ERROR |
|---|---|---|
| 38 (Claim 20, line 1) | 34 | delete the second occurrence of "wherein the" |

Signed and Sealed this

Sixth Day of March, 2007

JON W. DUDAS
*Director of the United States Patent and Trademark Office*